US012575728B2

(12) United States Patent
Fukuma et al.

(10) Patent No.: US 12,575,728 B2
(45) Date of Patent: Mar. 17, 2026

(54) FUNDUS OBSERVATION APPARATUS

(71) Applicant: Topcon Corporation, Tokyo (JP)

(72) Inventors: Yasufumi Fukuma, Wako (JP);
Yoshikiyo Moriguchi, Itabashi (JP)

(73) Assignee: TOPCON CORPORATION, Tokyo
(JP)

( * ) Notice: Subject to any disclaimer, the term of this
patent is extended or adjusted under 35
U.S.C. 154(b) by 318 days.

(21) Appl. No.: 18/197,754

(22) Filed: May 16, 2023

(65) Prior Publication Data

US 2023/0277055 A1 Sep. 7, 2023

Related U.S. Application Data

(63) Continuation of application No.
PCT/JP2021/044181, filed on Dec. 2, 2021.

(30) Foreign Application Priority Data

Dec. 9, 2020 (JP) ................................. 2020-203834

(51) Int. Cl.
*A61B 3/12* (2006.01)
*A61B 3/10* (2006.01)
*A61B 3/14* (2006.01)

(52) U.S. Cl.
CPC ................ *A61B 3/12* (2013.01); *A61B 3/102*
(2013.01); *A61B 3/1025* (2013.01); *A61B 3/14*
(2013.01)

(58) Field of Classification Search
CPC ......... A61B 3/12; A61B 3/102; A61B 3/1025;
A61B 3/14; A61B 3/1225

(Continued)

(56) References Cited

U.S. PATENT DOCUMENTS

| | | | |
|---|---|---|---|
| 7,831,106 | B2 | 11/2010 | Elsner et al. |
| 8,237,835 | B1 | 8/2012 | Muller |

(Continued)

FOREIGN PATENT DOCUMENTS

| | | |
|---|---|---|
| CN | 108371542 A | 8/2018 |
| EP | 3150109 A1 | 4/2017 |

(Continued)

OTHER PUBLICATIONS

Extended European Search Report issued Jan. 10, 2025, in corresponding European Patent Application No. 21903274.5, 16pp.

(Continued)

*Primary Examiner* — Mohammed A Hasan

(74) *Attorney, Agent, or Firm* — XSENSUS LLP

(57) ABSTRACT

A fundus observation apparatus includes an illumination optical system, a two-dimensional image sensor, and a deflecting member. The illumination optical system is configured to illuminate a fundus of a subject's eye with line-shaped illumination light. The two-dimensional image sensor is configured to receive returning light of the illumination light from the fundus on a movable focal plane at a position substantially conjugate optically to the fundus. The deflecting member is configured to couple an optical path of the illumination light and an optical path of the returning light and to scan the fundus with the illumination light by deflecting the illumination light in synchronization with a movement of the focal plane. The deflecting member has a configuration that allows the returning light to be transmitted through a first region and to reflect the illumination light in a second region different from the first region.

18 Claims, 25 Drawing Sheets

(58) Field of Classification Search
USPC .......................................................... 351/221
See application file for complete search history.

(56)                    References Cited

U.S. PATENT DOCUMENTS

| | | | |
|---|---|---|---|
| 2006/0228011 A1 | 10/2006 | Everett et al. | |
| 2007/0159595 A1* | 7/2007 | Fukuma ................. | A61B 3/102 |
| | | | 351/206 |
| 2010/0141895 A1 | 6/2010 | Cairns et al. | |
| 2010/0195048 A1* | 8/2010 | Hammer .............. | A61B 3/1025 |
| | | | 351/246 |
| 2012/0133888 A1* | 5/2012 | Gray .................... | A61B 3/1025 |
| | | | 351/221 |
| 2013/0222763 A1* | 8/2013 | Bublitz .................... | A61B 3/14 |
| | | | 351/246 |
| 2014/0118687 A1* | 5/2014 | Ohban ..................... | A61B 3/12 |
| | | | 351/246 |
| 2014/0232987 A1 | 8/2014 | Westphal et al. | |
| 2015/0116660 A1* | 4/2015 | Matsumoto .......... | A61B 3/0058 |
| | | | 351/206 |
| 2015/0131050 A1 | 5/2015 | Bublitz et al. | |
| 2015/0216408 A1 | 8/2015 | Brown et al. | |
| 2015/0272435 A1* | 10/2015 | Ito ............................ | A61B 3/14 |
| | | | 351/206 |
| 2017/0049323 A1 | 2/2017 | Bublitz et al. | |
| 2018/0289260 A1 | 10/2018 | Matsunobu et al. | |
| 2019/0117063 A1 | 4/2019 | Qiu et al. | |
| 2020/0000336 A1 | 1/2020 | Bublitz et al. | |
| 2020/0214557 A1 | 7/2020 | Hirose et al. | |
| 2021/0196116 A1 | 7/2021 | Yamaguchi et al. | |
| 2021/0275010 A1 | 9/2021 | Muyo et al. | |
| 2022/0211268 A1 | 7/2022 | Bublitz et al. | |

FOREIGN PATENT DOCUMENTS

| | | | |
|---|---|---|---|
| EP | 3679855 | A1 | 7/2020 |
| JP | 2009-543585 | A | 12/2009 |
| JP | 2011092290 | A | 5/2011 |
| JP | 2017-064219 | A | 4/2017 |
| JP | 2018-108400 | A | 7/2018 |
| JP | 2018-167000 | A | 11/2018 |
| WO | 2014/140256 | A2 | 9/2014 |
| WO | 2018069346 | A1 | 4/2018 |
| WO | 2018/088338 | A1 | 5/2018 |
| WO | 2020054280 | A1 | 3/2020 |

OTHER PUBLICATIONS

Extended European Search Report issued Feb. 25, 2025, in corresponding European Patent Application No. 24209971.1, 8pp.
International Search Report and Written Opinion mailed on Jan. 18, 2022, received for PCT Application PCT/JP2021/044181, filed on Dec. 2, 2021, 8 pages including English Translation.
Communication pursuant to Rule 164(1) EPC issued Oct. 7, 2024, in corresponding European Patent Application No. 21903274.5, 15pp.
Chinese Office Action issued Jan. 19, 2026, in corresponding Chinese Patent Application No. 202180082358.1, 16pp.
Japanese Office Action issued Jan. 20, 2026, in corresponding Japanese Patent Application No. 2022-189922, 6pp.
Japanese Office Action issued Jan. 20, 2026, in corresponding Japanese Patent Application No. 2022-568222, 9pp.

* cited by examiner

FUNDUS OBSERVATION APPARATUS

CROSS-REFERENCE TO RELATED APPLICATIONS

The present application is a continuation application of International Patent Application No. PCT/JP2021/044181, filed Dec. 2, 2021, which claims priority to Japanese Patent Application No. 2020-203834, filed Dec. 9, 2020, both of which are herein incorporated by reference in their entirety.

FIELD

The disclosure relates to a fundus observation apparatus.

BACKGROUND

There is a demand for fundus observation apparatuses capable of easily observing and imaging a fundus or the like of a subject's eye with a wide field of view for screening or treating eye diseases. Specifically, there is a demand for fundus observation apparatuses that can observe the fundus of the subject's eye at a wide angle of view of more than 80 degrees in a single imaging (shot). As such fundus observation apparatuses, scanning laser ophthalmoscopes (SLOs) are known. SLO is an apparatus configured to form an image of the fundus by scanning the fundus with light to detect returning light of the light with a light receiving device.

For example, Japanese Unexamined Patent Application Publication (Translation of PCT application) No. 2009-543585 discloses a scanning ophthalmoscope that can scan a retina at a wide angle by moving a two-dimensional collimated scan using a polygon mirror and a plane mirror on the subject's eye using a scan transfer means.

For example, U.S. Pat. No. 7,831,106 discloses a fundus imaging apparatus that can obtain high-contrast images with a simple configuration, by combining line scanning and rolling shutter.

Further, in recent years, attention has been drawn to optical coherence tomography (OCT) which is used to measure the morphology of an object to be measured or to image using light beam emitted from a laser light source or the like. Since OCT does not have invasiveness to human body as X-ray CT (Computed Tomography) does, development of application of OCT in medical field and biology field is particularly expected. Apparatuses using such OCT are applied to the diagnosis of various eye diseases, because of the ability to acquire high precision images.

For example, Japanese Unexamined Patent Publication No. 2018-108400 discloses an ophthalmic apparatus that combines an imaging function by SLO and a measurement function using OCT. Particularly, Japanese Unexamined Patent Publication No. 2018-108400 discloses a method of realizing the imaging function using SLO and the measurement function using OCT by sharing an optical scanner.

SUMMARY

One aspect of embodiments is a fundus including: an illumination optical system configured to illuminate a fundus of a subject's eye with line-shaped illumination light; a two-dimensional image sensor configured to receive returning light of the illumination light from the fundus on a movable focal plane at a position substantially conjugate optically to the fundus; and a deflecting member configured to couple an optical path of the illumination light and an optical path of the returning light and to scan the fundus with the illumination light by deflecting the illumination light in synchronization with a movement of the focal plane, wherein the deflecting member has a configuration that allows the returning light to be transmitted through a first region and to reflect the illumination light in a second region different from the first region.

Another aspect of the embodiments is a fundus observation apparatus, including: a fundus observation optical system configured to illuminate a fundus of a subject's eye with illumination light, and to receive returning light of the illumination light from the fundus using a two-dimensional image sensor; an OCT optical system including an optical scanner and configured to perform OCT scan that irradiates measurement light deflected by the optical scanner onto the subject's eye and detects interference light between returning light of the measurement light and reference light; and an optical path coupling separating member configured to couple an optical path of the returning light of the illumination light with an optical path of the OCT optical system, wherein the fundus observation optical system includes a deflecting member having a configuration that allows the returning light to be transmitted through a first region and to reflect the illumination light in a second region different from the first region, and having a scanning mechanism that scans the fundus with the illumination light by deflecting the illumination light, wherein the optical path coupling separating member is positioned between the deflecting member and the two-dimensional image sensor.

DETAILED DESCRIPTION

Figure 1:
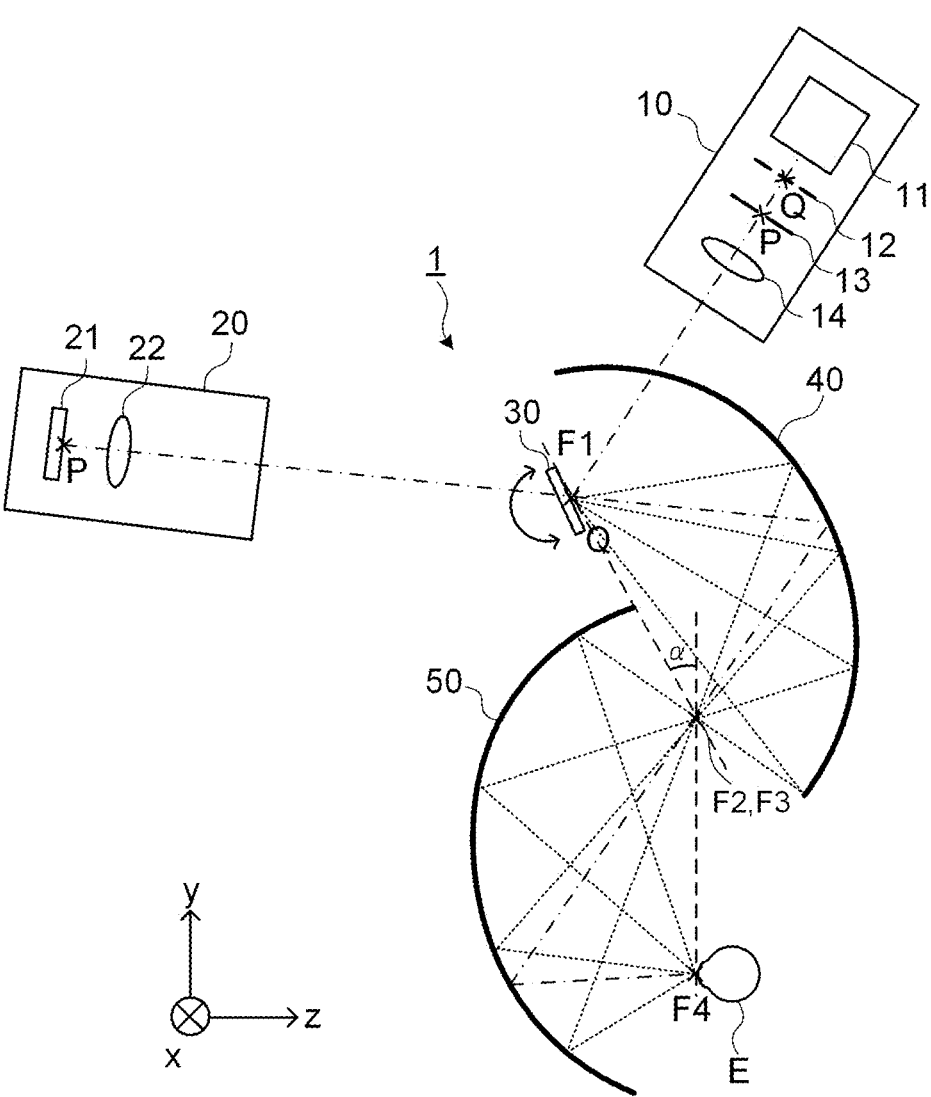
FIG. 1 is a schematic diagram illustrating an example of a configuration of an optical system of a fundus observation apparatus according to a first embodiment.

The method disclosed in Japanese Unexamined Patent Application Publication (Translation of PCT application) No. 2009-543585 requires a high speed scanner such as a polygon mirror. However, high speed scanners capable of scanning at wide angles are very expensive.

Further, in case of imaging the fundus at a wide angle, an optical path of an illumination light and an optical path of returning light of the illumination light should be coupled at a branch point at a position conjugate to a pupil of the subject's eye. In the method disclosed in U.S. Pat. No. 7,831,106, it is difficult to divide a line scanning optical system between a light source and the branch point, an observation optical system between the branch point and an image sensor, and a shared optical system shared between the illumination light and the returning light between the pupil of the subject's eye and the branch point. In particular, when the angle of view for imaging exceeds 80 degrees, it is very difficult in practical terms to keep the two light fluxes, that are an illumination flux in the line scanning optical system and a shared light flux in the shared optical system, within 180 degrees.

Further, in the method disclosed in Japanese Unexamined Patent Publication No. 2018-108400, the information acquisition time per point where the laser is irradiated differs greatly. Thereby, imaging ranges can be acquired within the same imaging time differs. In general, the measurement range acquired in a single OCT measurement (OCT imaging) is smaller than the imaging range acquired in a single imaging by SLO. Therefore, when an SLO optical system that realizes SLO imaging and an OCT optical system that realizes OCT measurement are optically coupled to perform observation in a wide-angle range, SLO imaging and OCT measurement cannot be performed in parallel in case of simply coupling the SLO optical system and the OCT optical system. In particular, when the optical scanner is shared between SLO imaging and OCT measurement, it becomes impossible to measure the desired site using OCT while observing the fundus at a wide angle.

As described above, a new technology for observing the fundus of the subject's eye at a wide angle with a low cost and simple configuration is desired. In this case, it is desirable to be capable of performing OCT measurement while observing the fundus of the subject's eye at wide angle.

According to some embodiments of the present invention, a new technique for observing a fundus of a subject's eye at a wide angle with a low cost and simple configuration can be provided.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Referring now to the drawings, exemplary embodiments of a fundus observation apparatus according to the present invention are described below. Any of the contents of the documents cited in the present specification and arbitrary known techniques may be applied to the embodiments below.

The term "processor" as used herein refers to a circuit such as, for example, a central processing unit (CPU), a graphics processing unit (GPU), an application specific integrated circuit (ASIC), and a programmable logic device (PLD). Examples of PLD include a simple programmable logic device (SPLD), a complex programmable logic device (CPLD), and a field programmable gate array (FPGA). The processor realizes, for example, the function according to the embodiments by reading out a computer program stored in a storage circuit or a storage device and executing the computer program.

A fundus observation apparatus according to embodiments is configured to illuminate a fundus of a subject's eye with illumination light whose cross-sectional luminous flux shape is a line shape, and to receive returning light of the illumination light from the fundus on a movable focal plane at a position substantially conjugate optically to the fundus. In this case, an optical path of the illumination light and an optical path of the returning light are coupled (separated) using a deflecting member. Here, the deflecting member has a configuration that allows the returning light to be transmitted through (pass through) a first region (for example, a region including a central part) of the deflecting member and to reflect the illumination light in (on) a second region (for example, a peripheral region (region including the peripheral region) of the region including the central region) of the deflecting member, the second region being different from the first region. And, the fundus is scanned with the illumination light by deflecting the illumination light using the deflecting member in synchronization with a movement of the focal plane. In some embodiments, the first region is a peripheral region of the region including the central part of the deflecting member, and the second region is the region including the central region of the deflecting member. The first region may be a region that does not overlap with the second region. In some embodiments, an optical path coupling part between the optical path of the illumination light and the optical path of the returning light in the deflecting member is positioned at a position substantially conjugate optically to a pupil of the subject's eye. In some embodiments, the deflecting member is a hole mirror.

Thereby, a shared optical system shared between the optical path of the wide-angle illumination light and the optical path of the returning light can be easily arranged while ensuring an angle of view for imaging of more than 80 degrees with the optical system alone that scans in a width direction of a line of the illumination light.

In some embodiments, the fundus observation apparatus includes an OCT optical system including an optical scanner. Here, the OCT optical system is configured to irradiate measurement light deflected by the optical scanner onto the subject's eye and to perform OCT scan that detects interference light between returning light of the measurement light and reference light. In this case, the optical path of the returning light of the line-shaped illumination light and an optical path of the OCT optical system are coupled by an optical path coupling separating member arranged between the deflecting member and two-dimensional image sensor. In other words, by optically coupling the OCT optical system with the optical path of the returning light on the transmission side of the deflecting member (through a hole in the hole mirror), the optical path of the returning light of the illumination light can be separated from the above shared optical system at low cost. Further, OCT measurement (OCT imaging) can be performed on any position on the fundus being observed at a large wide angle, without sharing an optical scanner for OCT scanning and an optical scanner for deflection of illumination light.

Hereinafter, a case where the fundus observation apparatus according to the embodiments acquires images of the fundus of the subject's eye using an ellipsoidal mirror (a concave mirror in a broad sense) as an aspheric mirror will be mainly described. Further, a case where the deflecting member has a configuration that allows the returning light to be transmitted through (pass through) a region including the central part as the first region and to reflect the illumination light in the peripheral region of the region including the central part as the second region will be described.

First Embodiment

<Configuration>

FIG. 1 illustrates an example of a configuration of an optical system of the fundus observation apparatus according to a first embodiment. In FIG. 1, a position substantially conjugate optically to a fundus Ef of a subject's eye E is illustrated as a fundus conjugate position P, and a position substantially conjugate optically to a pupil (iris) of the subject's eye E is illustrated as a pupil (iris) conjugate position Q.

The fundus observation apparatus 1 according to the first embodiment includes a slit projection optical system 10, a slit light receiving optical system 20, a hole mirror 30 as a deflecting member having a scanning mechanism, a first ellipsoidal mirror 40, and a second ellipsoidal mirror 50.
(Slit Projection Optical System 10)

The slit projection optical system 10 generates slit-shaped illumination light (illumination light whose luminous flux cross-sectional shape is a line shaped), and projects the generated illumination light onto the hole mirror 30. The slit projection optical system 10 includes an illumination light source 11, an iris aperture 12, a slit 13, and a projection lens 14.

The illumination light source 11 includes a visible light source that generates light in the visible region. For example, the illumination light source 11 generates light having a central wavelength in the wavelength range of 420 nm to 700 nm. This type of illumination light source 11 includes, for example, an LED (Light Emitting Diode), an LD (Laser Diode), a halogen lamp, or a xenon lamp. In some embodiments, the illumination light source 11 includes a white light source or a light source capable of outputting light with each color component of RGB. In some embodiments, the illumination light source 11 includes a light source capable of switching to output the light in infrared region or the light in visible region. The illumination light source 11 is arranged at a position non-conjugate optically to the fundus Ef of the subject's eye E and an iris of the subject's eye E, respectively.

The iris aperture 12 (specifically, aperture(s) described below) can be arranged at the pupil conjugate position Q. In the iris aperture 12, one or more apertures are formed at position(s) away from an optical axis of an optical path of light output from the illumination light source 11. The aperture formed in the iris aperture 12 defines an incident position (incident shape) of the illumination light on the iris of the subject's eye E. For example, apertures are formed at point-symmetric positions centered on the optical axis. Thereby, when the pupil center of the subject's eye E is arranged on the optical axis of the optical path of the illumination light, the illumination light can enter into the eye from positions eccentric from the pupil center (specifically, point-symmetrical positions centered on the pupil center).

Further, the light amount distribution of the light passing through the aperture(s) formed in the iris aperture 12 can be changed by changing a relative position between the illumination light source 11 and the aperture(s) formed in the iris aperture 12.

The slit 13 (specifically, aperture(s) described below) can be arranged at the fundus conjugate position P. The aperture formed in the slit 13 defines a shape of an irradiated region (irradiated pattern shape) of the illumination light on the fundus Ef of the subject's eye E.

The slit 13 can be moved in an optical axis direction of the slit projection optical system 10 using a movement mechanism (not shown). The movement mechanism moves the slit 13 in the optical axis direction, under the control from a controller described below. This allows to move the position of the slit 13 in accordance with the state of the subject's eye E (specifically, the dioptric power or the shape of the fundus Ef).

In some embodiments, the slit 13 is configured so that at least one of the position of the aperture and the shape of the aperture can be changed in accordance with the state of the subject's eye E without being moved in the optical axis direction. The function of the slit 13 with this configuration is, for example, realized by a liquid crystal shutter.

The light from the illumination light source 11 that has passed through the aperture(s) formed in the iris aperture 12 passes through the aperture(s) formed in the slit 13, is transmitted through the projection lens 14, and is output as the slit-shaped illumination light. The slit-shaped illumination light output from slit projection optical system 10 is guided to the hole mirror 30.

In some embodiments, the slit projection optical system 10 includes a projector with a light source, and the projector outputs the slit-shaped illumination light. Examples of the projector include an LCD (Liquid Crystal Display) type projector using a transmissive LCD panel, an LCOS (Liquid Crystal On Silicon) type projector using a reflective LCD panel, a DLP (Digital Light Processing) (registered trademark) type projector using a DMD (Digital Mirror Device).
(Hole Mirror 30)

The hole mirror 30 (specifically, deflection surface described below) can be arranged at the pupil conjugate position Q. The hole mirror 30 has a deflection surface whose orientation (deflection direction) can be changed and functions as a uniaxial optical scanner that guides the illumination light from the slit projection optical system 10 to a reflective surface of the first ellipsoidal mirror 40 described below. The hole is formed in the deflection surface so that the optical axis of the slit light receiving optical system 20 described below passes through it. In other words, the hole mirror 30 has a configuration that allows the returning light of the illumination light to be transmitted through (pass through) the central part and to reflect the illumination light in a peripheral part of the central part.

The hole mirror 30 deflects the illumination light by changing the orientation of the deflection surface so that the irradiated region moves sequentially in a direction (direction of the slit width, shorter direction of the irradiated region) orthogonal to a slit direction (direction in which the slit extends, longitudinal direction of the irradiated region) of the irradiated region at an irradiated site of the illumination light on the subject's eye E. The hole mirror 30 is configured to be capable of changing the deflection direction of the illumination light, under the control from the controller described below.

The illumination light from the slit projection optical system 10 is deflected on the deflection surface around the hole and is guided to the reflective surface of the first ellipsoidal mirror 40. The returning light of the illumination light from the subject's eye E passes through the hole formed in the hole mirror 30 via the reflective surface of the first ellipsoidal mirror 40 and is guided to the slit light receiving optical system 20.

In some embodiments, the hole mirror 30 is configured to transmit the wavelength component (or polarization component) of the returning light of the illumination light. In this case, the returning light of the illumination light from the subject's eye E is transmitted through the hole mirror 30 via the reflective surface of the first ellipsoidal mirror 40, and is guided to the slit light receiving optical system 20.
(Slit Light Receiving Optical System 20)

The slit light receiving optical system 20 receives the returning light of the illumination light from the subject's eye E that has passed through the hole of the hole mirror 30. The slit light receiving optical system 20 includes an image sensor 21 and an imaging lens 22.

The image sensor 21 realizes the function of the two-dimensional image sensor as a pixelated photodetector. The light receiving surface (detecting surface, imaging surface) of the image sensor 21 can be arranged at the fundus conjugate position P. The image sensor 21 is configured to be set an opening range (focal plane) that can be moved at the fundus conjugate position P.

For example, the light receiving result(s) acquired by the image sensor 21 is/are read out using a rolling shutter method. In some embodiments, the controller described below performs readout control of the light receiving result(s) by controlling the image sensor 21. In some embodiments, the image sensor 21 can automatically output the light receiving result(s) for a predetermined number of lines, along with information indicating the light receiving position(s).

The image sensor 21 with such a configuration includes a CMOS (Complementary metal oxide semiconductor) image sensor. In this case, the image sensor 21 includes a plurality of pixels (light receiving elements). The plurality of pixels includes a plurality of pixel groups arranged in a column direction. Each of the plurality of pixel groups includes pixels arranged in a row direction. Specifically, the image sensor 21 includes a plurality of pixels arranged two-dimensionally, a plurality of vertical signal lines, and a horizontal signal line. Each pixel includes a photodiode (light receiving element), and a capacitor. The vertical signal lines are provided for each pixel group in the column direction (vertical direction) orthogonal to the row direction (horizontal direction). Each of the vertical signal lines is selectively electrically connected to the pixel group in which the electrical charge corresponding to the light receiving result is accumulated. The horizontal signal line is selectively electrically connected to the vertical signal lines. Each of the pixels accumulates the electrical charge corresponding to the light receiving result of the returning light. The accumulated electrical charge is read out sequentially for each pixel group in the row direction, for example. For example, for each line in the row direction, a voltage corresponding to the electrical charge accumulated in each pixel is supplied to the vertical signal line. The vertical signal lines are selectively electrically connected to the horizontal signal line. By performing readout operation for each line in the row direction described above sequentially in the vertical direction, the light receiving results of the plurality of pixels arranged two-dimensionally can be read out.

By capturing (reading out) the light receiving results of the returning light using the rolling shutter method for this type of image sensor 21, the light receiving image corresponding to the desired virtual opening shape extending in the row direction is acquired. Such control is disclosed in, for example, U.S. Pat. No. 7,831,106 or U.S. Pat. No. 8,237,835.

The imaging lens 22 forms an image of the returning light of the illumination light that has passed through the hole formed in the hole mirror 30 (or returning light of the illumination light that has been transmitted through the hole mirror 30) on the light receiving surface of the image sensor 21.

(First Ellipsoidal Mirror 40)

The reflective surface (first reflective surface) of the first ellipsoidal mirror 40 is an elliptical surface. The first ellipsoidal mirror 40 is an example of the concave mirror.

The first ellipsoidal mirror 40 has two optically conjugate focal points (first focal point F1, second focal point F2). The hole mirror 30 (deflection surface of the hole mirror 30) is positioned at the first focal point F1 of the first ellipsoidal mirror 40 or near the first focal point F1. In some embodiments, the hole mirror 30 is positioned at a position conjugate optically to the first focal point F1 (conjugate position of the first focal point F1) or near the position.

(Second Ellipsoidal Mirror 50)

The reflective surface (second reflective surface) of the second ellipsoidal mirror 50 is an elliptical surface. The second ellipsoidal mirror 50 is an example of the concave mirror.

The second ellipsoidal mirror 50 has two optically conjugate focal points (first focal point F3, second focal point F4). The second ellipsoidal mirror 50 is arranged so that the first focal point F3 substantially coincides with the second focal point F2 of the first ellipsoidal mirror 40. In some embodiments, the second ellipsoidal mirror 50 is arranged so that the first focal point F3 substantially coincides with a position conjugate optically to the second focal point F2 of the first ellipsoidal mirror 40 (conjugate position of the second focal point F2) or near the position. The subject's eye E is arranged at the second focal point F4 of the second ellipsoidal mirror 50. In other words, the second ellipsoidal mirror 50 is arranged so that the second focal point F4 substantially coincides with a subject's eye position where the subject's eye is arranged.

Thus, a scanning optical member does not need to be disposed at the second focal point F2 (first focal point F3) between the first ellipsoidal mirror 40 and the second ellipsoidal mirror 50. Therefore, the scan range in a predetermined scan direction (lateral direction, horizontal direction) is not limited. For example, in the configuration described in Japanese Unexamined Patent Application Publication (Translation of PCT application) No. 2009-543585, a deflecting member is provided for scanning the illumination light in the lateral direction, which theoretically allows an angle of view for imaging of up to 180 degrees (realistically, up to about 150 degrees). In contrast, according to the embodiments, the deflecting member for scanning in the lateral direction does not need to be disposed. Therefore, imaging up to an angle of view beyond 180 degrees becomes possible (since the cornea of the human eye is positioned at a position projected forward from the pupil, it is possible to observe an range beyond 180 degrees with a fisheye lens-like effect).

The second ellipsoidal mirror 50 is arranged so that an angle between a straight line connecting the first focal point F1 and the second focal point F2 of the first ellipsoidal mirror 40 and a straight line connecting the first focal point F3 and the second focal point F4 of the second ellipsoidal mirror 50 is an angle α. For example, the angle α is 30 degrees. In some embodiments, the second ellipsoidal mirror 50 is configured to be movable relative to the first ellipsoidal mirror 40 so as to change the angle α.

In such a configuration, the illumination light deflected by the hole mirror 30 arranged at the first focal point F1 is reflected on the reflective surface of the first ellipsoidal mirror 40 and is guided to the second focal point F2 of the first ellipsoidal mirror 40. The illumination light that has been guided to the second focal point F2 is guided to the reflective surface of the second ellipsoidal mirror 50, is reflected on this reflective surface, and is guided to the subject's eye E arranged at the second focal point F4 of the second ellipsoidal mirror 50.

The illumination light that has been guided to the subject's eye E enters the eye through the pupil and is irradiated onto the fundus Ef. The returning light of the illumination light reflected on the fundus Ef is emitted outside of the subject's eye E through the pupil, travels in the same path as the outward path in the opposite direction, and is guided to the first focal point F1 of the first ellipsoidal mirror 40. The returning light of the illumination light that has been guided to the first focal point F1 passes through the hole formed in the hole mirror 30 (or is transmitted through the hole mirror 30), and is guided to the slit light receiving optical system 20, as described above.

In some embodiments, at least one of the first ellipsoidal mirror 40 and the second ellipsoidal mirror 50 is a concave mirror whose reflective surface is formed in a concave shape. In some embodiments, the reflective surface of the concave mirror is formed to be a free-form surface.

In addition to the configuration shown in FIG. 1, the fundus observation apparatus 1 may be provided with an alignment optical system for performing position matching between the subject's eye E and the optical system. The fundus observation apparatus 1 may be provided with a focusing mechanism using the movement of the lens or the movement of the slit light receiving optical system 20.

Further, the fundus observation apparatus 1 may have a configuration for providing a function associated with the inspection. For example, the fundus observation apparatus 1 may be provided with a fixation optical system for projecting a visual target (fixation target) for fixating the subject's eye E onto the fundus Ef of the subject's eye E. Further, the fundus observation apparatus 1 may be provided with any element or unit, such as a member for supporting the face of the subject (chin rest, forehead pad, etc.).

Figure 2:
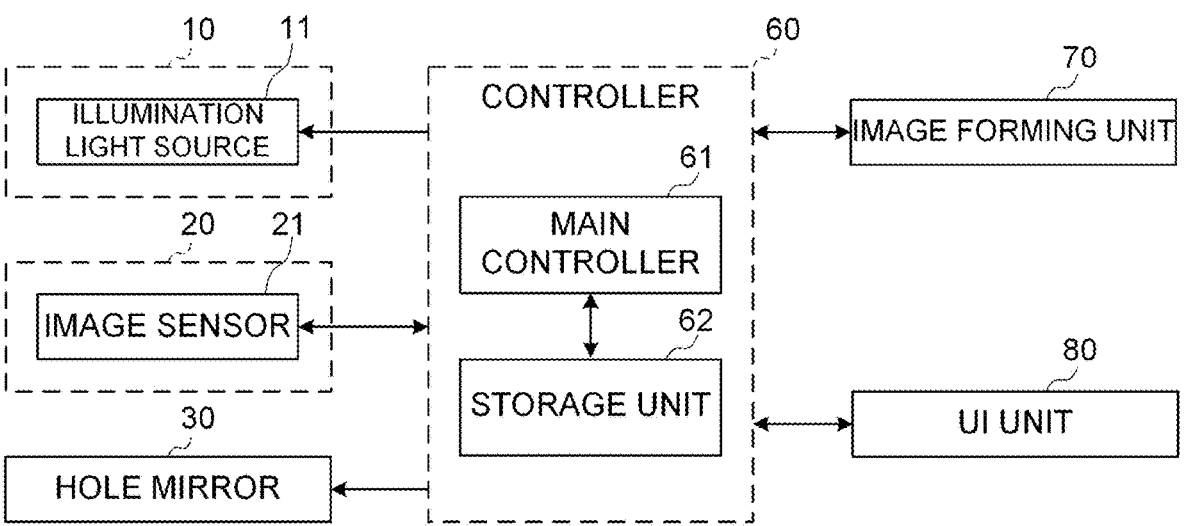
FIG. 2 is a schematic diagram illustrating an example of a configuration of a processing system of the fundus observation apparatus according to the first embodiment.

FIG. 2 illustrates an example of a configuration of a processing system of the fundus observation apparatus 1 according to the first embodiment. In FIG. 2, like reference numerals designate like parts as in FIG. 1. The same description may not be repeated.

The processing system of the fundus observation apparatus 1 is configured with the controller 60 as a center. The controller 60 controls each part of the fundus observation apparatus 1.

The controller 60 includes a main controller 61 and a storage unit 62. The functions of the main controller 61 are realized by a processor, for example. The storage unit 62 stores, in advance, computer programs for controlling the fundus observation apparatus 1. Examples of the computer programs include an illumination light source control program, an image sensor control program, a hole mirror control program, an image forming program, program for user interface. The main controller 61 operates according to the computer programs, and thereby the controller 60 performs the control processing.

(Main Controller 61)

The main controller 61 controls each of the slit projection optical system 10, the a slit light receiving optical system 20, the hole mirror 30, the image forming unit 70, and the user interface (UI) unit 80.

Examples of the control for the slit projection optical system 10 include control for the illumination light source 11. Examples of the control for the illumination light source 11 include turning the light source on and off, adjustment of the light amount, adjustment of an aperture.

Examples of the control for the slit light receiving optical system 20 include control for the image sensor 21. Examples of the control for the image sensor 21 include control of setting the opening range (focal plane) that can be moved at the fundus conjugate position P and control for reading out the light receiving result(s) using a rolling shutter method (for example, setting of light receiving size corresponding to the size of the illumination pattern, or the like). Further, the control for the image sensor 21 includes the reset control, the exposure control, the charge transfer control, and the output control.

Examples of the control for the hole mirror 30 include control of the angle of the deflection surface for deflecting the illumination light. By controlling the angle of the deflection surface, the deflection direction of illumination light can be controlled. By controlling an angle range of the deflection surface, the scan range (scan start position and scan end position) can be controlled. By controlling the speed of changing the angle of deflection surface, the scan speed can be controlled.

Examples of the control for the image forming unit 70 include image forming control for forming images of the subject's eye E from the light receiving result(s) obtained using the image sensor 21.

Examples of the control for the UI unit 80 include a control for a display device and a control for an operation device (input device).

(Storage Unit 62)

The storage unit 62 stores various types of data. Examples of the data stored in the storage unit 62 include light receiving result(s) obtained by the image sensor 21, image data of an image formed by the image forming unit 70, and subject's eye information. The subject's eye information includes information on the subject such as patient ID and name, and information on the subject's eye such as identification information of the left eye/right eye.

The storage unit 62 further stores various types of programs and data to run the fundus observation apparatus 1.

(Image Forming Unit 70)

The image forming unit 70 can form the light receiving image (fundus image) corresponding to the arbitrary opening range (focal plane) based on the light receiving result(s) read out from the image sensor 21 using the rolling shutter method. The image forming unit 70 can sequentially form light receiving light images corresponding to the opening ranges and form an image of the subject's eye E from a plurality of formed light receiving images. The various images (the various image data) formed by the image forming unit 70 are stored in the storage unit 62, for example.

For example, the image forming unit 70 includes a processor, and executes the function described above by performing processing corresponding to the program(s) stored in the storage unit or the like.

(UI Unit 80)

The UI unit 80 has a function for exchanging information between a user and the fundus observation apparatus 1. The UI unit 80 includes the display device and the operation device. The display device may include a display unit, and it may include another display device. The display device displays various information. The display device includes a liquid crystal display, for example. The display device displays the above information under the control of the main controller 61. Examples of the information displayed on the display device include information corresponding to the control result by the controller 60, information (image) corresponding to the calculation result by the image forming unit 70. The operation device includes various hardware keys and/or various software keys. Upon receiving the operation content for the operation device, the main controller 61 can output a control signal corresponding to the operation content to each part of the fundus observation apparatus. At least a part of the display device and at least a part of the operation device may be configured integrally. One example of this is the touch panel display.

The slit projection optical system 10 is an example of the "illumination optical system" according to the embodiments. The image sensor 21 is an example of the "two-dimensional image sensor" according to the embodiments. The hole mirror 30 is an example of the "deflecting member" according to the embodiments. The first ellipsoidal mirror 40 is an example of the "first concave mirror" according to the embodiments. The second ellipsoidal mirror 50 is an example the "second concave mirror" according to the embodiments.

<Operation>

Next, the operation of the fundus observation apparatus 1 according to the first embodiment will be described.

Figure 3:
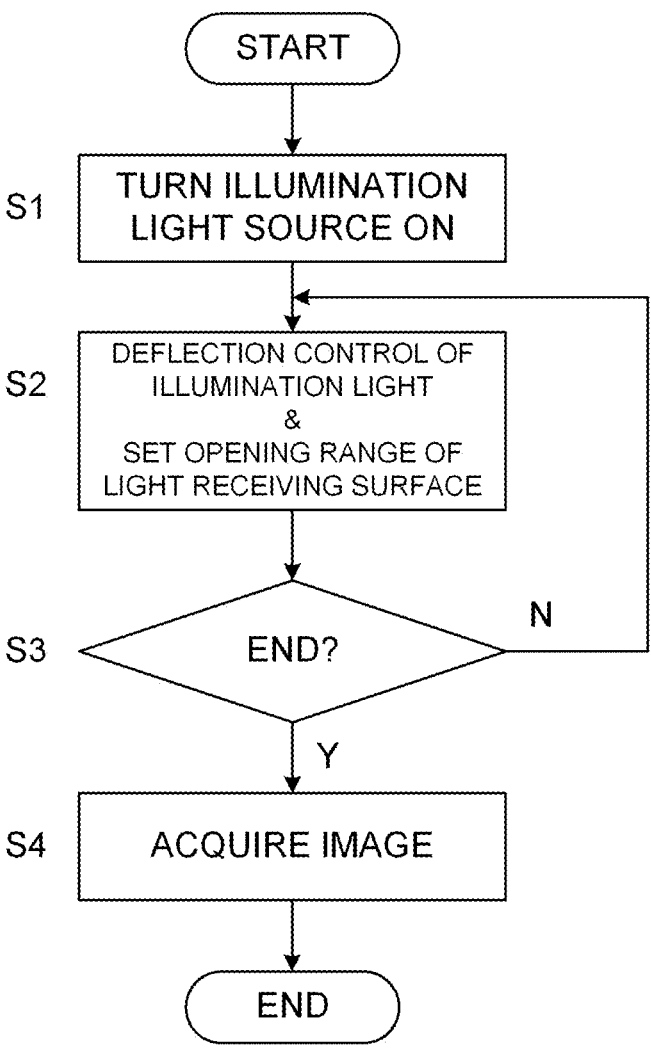
FIG. 3 is a flowchart illustrating an example of an operation of the fundus observation apparatus according to the first embodiment.

FIG. 3 shows an example of the operation of the fundus observation apparatus 1 according to the first embodiment. FIG. 3 represents a flowchart of an example of the operation of the fundus observation apparatus 1 according to the first embodiment. The storage unit 62 stores computer programs for realizing the processing shown in FIG. 3. The main controller 61 operates according to the computer programs, and thereby the main controller 61 performs the processing shown in FIG. 3.

It is assumed that the subject's eye E is arranged at a predetermined subject's eye position (the second focal point F4 of the second ellipsoidal mirror 50 in FIG. 1), in FIG. 3.

(S1: Turn Illumination Light Source On)

The main controller 61 controls the illumination light source 11 to turn the illumination light source 11 on.

The light output from the illumination light source 11 passes through the aperture(s) formed in the iris aperture 12, passes through the aperture(s) formed in the slit 13, is transmitted through the projection lens 14, and is guided to the hole mirror 30 as the slit-shaped illumination light.

(S2: Deflection Control of Illumination Light and Set Opening Range of Light Receiving Surface)

Subsequently, the main controller 61 controls the hole mirror 30 to set the orientation of the deflection surface in a predetermined deflection direction in order to illuminate a predetermined irradiated range, and starts deflection control of the illumination light that sequentially changes the orientation of the deflection surface within a predetermined deflection angle range. In other words, the main controller 61 starts scanning the illumination light onto the fundus Ef.

In some embodiments, the main controller 61 controls the hole mirror 30 to perform deflection control of the illumination light in synchronization with the movement of the opening range that can be set in the image sensor 21.

In some embodiments, the main controller 61 controls the image sensor 21 to set the opening range including a light receiving range of the returning light on the light receiving surface corresponding to the irradiated region of the illumination light on the fundus Ef. For example, the irradiated range of the illumination light on the fundus Ef can be identified based on the deflection angle of the deflection surface of the hole mirror 30. The main controller 61 can set the opening range on the light receiving surface of the image sensor 21 corresponding to the deflection direction of the deflection surface of the hole mirror 30 that is changed sequentially.

The illumination light guided to the hole mirror 30 is deflected on the deflection surface whose deflection direction has been changed to guide to the reflective surface of the first ellipsoidal mirror 40, is reflected on this reflective surface, and is guided to the reflective surface of the second ellipsoidal mirror 50 via the second focal point F2 of the first ellipsoidal mirror 40. The illumination light guided to the reflective surface of the second ellipsoidal mirror 50 is reflected on this reflective surface, enters the eye of the subject's eye E arranged at the second focal point F2 of the second ellipsoidal mirror 50, and is irradiated onto the fundus Ef. The returning light of the illumination light from the fundus Ef travels in the same path as the outward path in the opposite direction, passes through the hole formed in the hole mirror 30 or is transmitted through the hole mirror 30, and is received on the light receiving surface of the image sensor 21 through the imaging lens 22. On the light receiving surface of image sensor 21, the opening range is set so as to include the light receiving range of the returning light corresponding to the irradiated range of the illumination light on the fundus Ef. Thereby, the returning light alone from fundus Ef can be received while suppressing the effect of unnecessary scattered light.

(S3: End?)

Subsequently, the main controller 61 determines whether or not to end the scanning of the illumination light for the fundus Ef. For example, the main controller 61 can determine whether or not to end the scanning of the illumination light for the fundus Ef, by determining whether or not the deflection angle of the deflection surface of the hole mirror 30, which is changed sequentially, is within the predetermined deflection angle range.

When it is determined to end the scanning of the illumination light for the fundus Ef (S3: Y), the operation of the fundus observation apparatus 1 proceeds to step S4. When it is determined not to end the scanning of the illumination light for the fundus Ef (S3: N), the operation of the fundus observation apparatus 1 proceeds to step S2.

(S4: Acquire Image)

When it is determined in step S3 to end the scanning of the illumination light for the fundus Ef (S3: Y), the main controller 61 controls the image forming unit 70 to form an image of the subject's eye based on the light receiving result(s) read out from the image sensor 21. In some embodiments, the image forming unit 70 sequentially forms the light receiving images based on the light receiving results read from the image sensor 21 in step S2, and forms an image of the subject's eye E from the plurality of formed light receiving images.

This ends the operation of the fundus observation apparatus 1 (END).

As explained above, according to the first embodiment, the optical path of the slit projection optical system 10 and the optical path of the slit light receiving optical system 20 are coupled using the hole mirror 30, and the illumination light is deflected and is guided to the reflective surface of the first ellipsoidal mirror 40 using the hole mirror 30. Thereby, a shared optical system shared between the optical path of the wide-angle illumination light and the optical path of the returning light can be easily arranged while ensuring an angle of view for imaging of more than 80 degrees with the optical system alone that scans in a slit width direction (width direction of a line) perpendicular to the slit direction of the illumination light, with a low cost and simple configuration. Further, the optical system can also be arranged on the passing (transmitting) side of the hole in the hole mirror 30. Therefore, the configuration does not require a pupil relay system, thereby increasing the degree of freedom in the arrangement of the optical system.

Furthermore, the deflection angle range can be widened while achieving quiet sound, by using the hole mirror 30 instead of a polygon mirror or the like. In addition, by making the scan length variable, the scan range of the illumination light can be set as desired.

Second Embodiment

The configuration of the fundus observation apparatus according to the embodiments is not limited to the configuration of the fundus observation apparatus 1 according to the first embodiment. For example, the fundus observation apparatus 1 according to the first embodiment may further be provided with an OCT optical system.

Hereinafter, in the embodiments, a case of using the swept source type OCT method in the measurement or the imaging (shooting) using OCT will be described. However, the configuration according to the embodiments can also be applied to a fundus observation apparatus using other type of OCT (for example, spectral domain type OCT).

In the following, the fundus observation apparatus according to a second embodiment will be described focusing on differences from the fundus observation apparatus 1 according to the first embodiment.

<Configuration>

Figure 4:
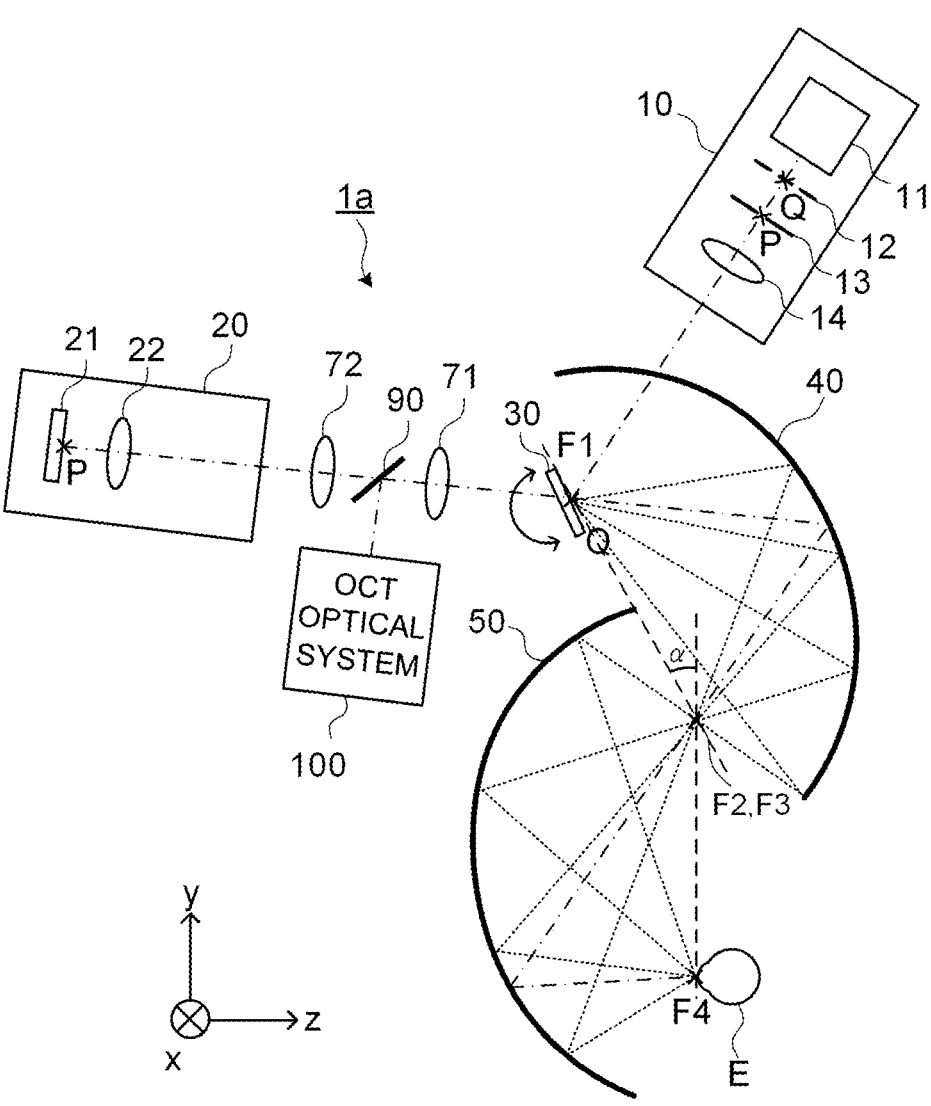
FIG. 4 is a schematic diagram illustrating an example of a configuration of an optical system of the fundus observation apparatus according to a second embodiment.

FIG. 4 shows an example of a configuration of an optical system of the fundus observation apparatus according to the second embodiment. In FIG. 4, like reference numerals designate like parts as in FIG. 1. The same description may not be repeated.

The configuration of the optical system in the fundus observation apparatus 1a according to the second embodiment differs from that of the optical system in the fundus observation apparatus 1 according to the first embodiment in that an OCT optical system 100 is added to the configuration of the optical system in the fundus observation apparatus 1. The optical path of the OCT optical system 100 is coupled with the optical path of the slit light receiving optical system 20 in the optical path between the slit light receiving optical system 20 and the hole mirror 30.

Specifically, a relay lens optical system including relay lenses 71 and 72 is arranged in the optical path between the slit light receiving optical system 20 and the hole mirror 30. The optical path between the relay lens 71 and the relay lens 72 is converted into an optical path of a telecentric optical system, and a dichroic mirror 90 is arranged in the optical path of the telecentric optical system. In other words, the relay lens optical system converts at least part of the optical path where the dichroic mirror 90 is arranged into the optical path of the telecentric optical system.

The dichroic mirror 90 is an optical path coupling separating member that separates the optical path of the OCT optical system 100 from the slit light receiving optical system 20 (or that couples the optical path of the slit light receiving optical system 20 and the optical path of the OCT optical system 100). The dichroic mirror 90 reflects the measurement light from the OCT optical system 100 to guide the measurement light to the relay lens 71, and reflects the returning light of the measurement light from subject's eye E to guide the returning light to the OCT optical system 100. Further, the dichroic mirror 90 transmits the returning light of the illumination light from the subject's eye E that has been guided through the relay lens 71 and guides the returning light to the relay lens 72.

(OCT Optical System 100)

Figure 5:
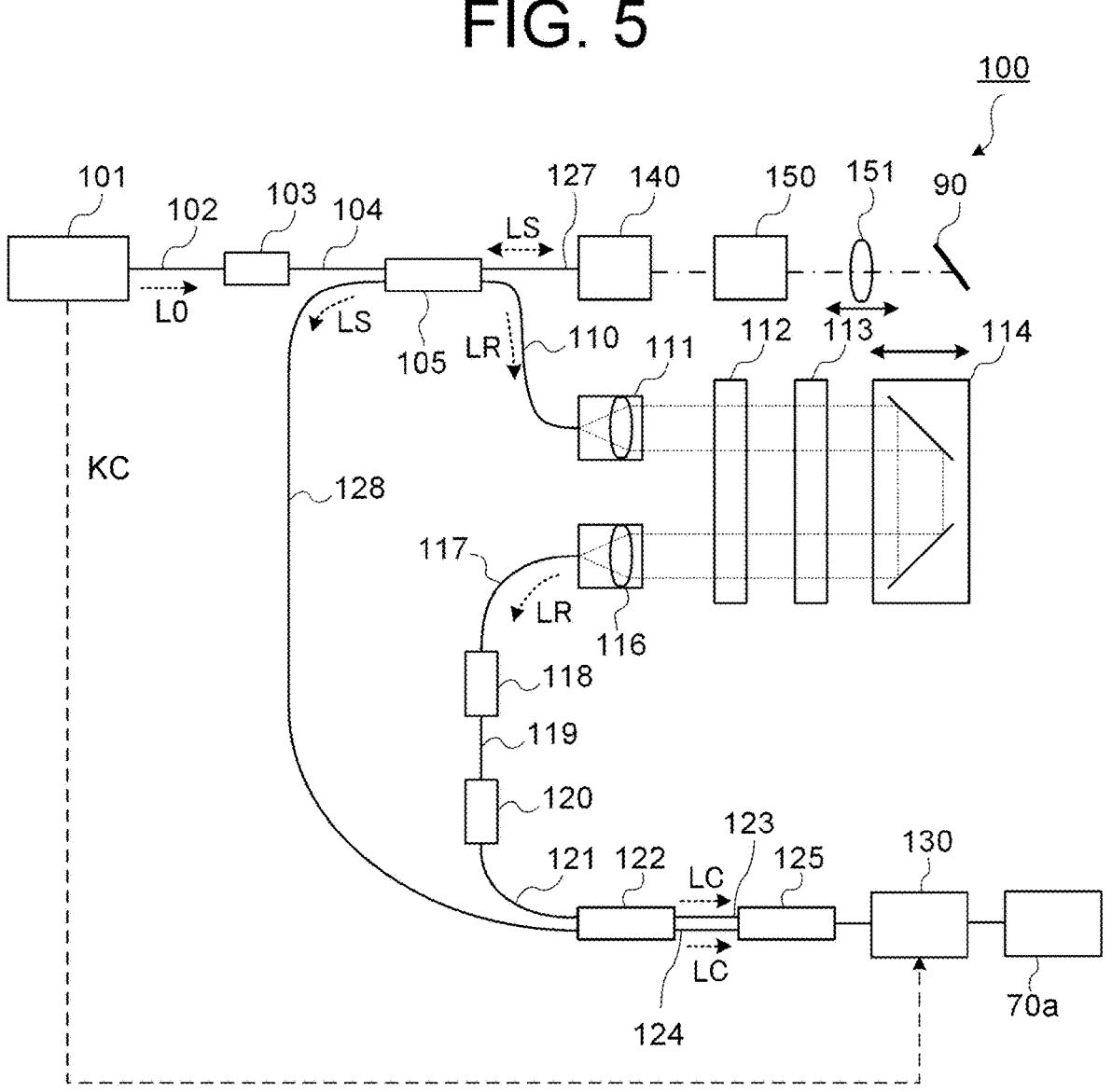
FIG. 5 is a schematic diagram illustrating an example of a configuration of an optical system of the fundus observation apparatus according to the second embodiment.

FIG. 5 shows an example of the configuration of the OCT optical system 100 in FIG. 4. In FIG. 5, parts similar to those in FIG. 4 are denoted by the same reference symbols, and description thereof is omitted as appropriate.

The OCT optical system 100 is provided with an optical system for performing OCT measurement (or OCT imaging) on the subject's eye E. This optical system is an interference optical system that splits light from a wavelength sweeping type (i.e., a wavelength scanning type) light source into measurement light and reference light, makes the measurement light returning from the subject's eye E and the reference light having traveled through the reference optical path interfere with each other to generate interference light, and detects the interference light. The detection result (detection signal) of the interference light obtained by the interference optical system is a signal indicating a spectrum of the interference light, and is sent to the image forming unit 70a, the data processor 75a, and the like which are described later.

Like swept source type fundus observation apparatuses commonly used, the OCT light source 101 includes a wavelength sweeping type (i.e., a wavelength scanning type) light source capable of sweeping (scanning) the wavelengths of emitted light. A laser light source including a resonator and emitting light having a center wavelength of 1050 nm, for example, is used as the wavelength sweeping type light source. The OCT light source 101 temporally changes the output wavelength in the near infrared wavelength band which cannot be visually recognized by the human eye.

Light L0 output from the OCT light source 101 is guided to the polarization controller 103 through the optical fiber 102, and the polarized wave state of the light L0 is adjusted. The polarization controller 103, for example, applies external stress to the looped optical fiber 102 to thereby adjust the polarization state of the light L0 guided through the optical fiber 102.

The light L0 whose the polarization state has been adjusted by the polarization controller 103 is guided to the fiber coupler 105 through the optical fiber 104, and is split into the measurement light LS and the reference light LR.

The reference light LR is guided to the collimator 111 through the optical fiber 110. The reference light LR is converted into a parallel light flux by the collimator 111. Then, the reference light LR is guided to the optical path length changing unit 114 via an optical path length correction member 112 and a dispersion compensation member 113. The optical path length correction member 112 acts so as to match the optical path length of the reference light LR with the optical path length of the measurement light LS. The dispersion compensation member 113 acts so as to match the dispersion characteristics between the reference light LR and the measurement light LS.

The optical path length changing unit 114 is movable in directions indicated by the arrow in FIG. 5, thereby changing the length of the optical path of the reference light LR. Through such movement, the length of the optical path of the reference light LR is changed. The change in the optical path length is used for the correction of the optical path length according to the axial length of the subject's eye E, and/or for the adjustment of the interference state, or the like. The optical path length changing unit 114 includes, for example, a corner cube and a movement mechanism for moving the corner cube. In this case, the corner cube in the optical path length changing unit 114 changes the traveling direction of the reference light LR that has been made into the parallel light flux by the collimator 111 in the opposite direction. The optical path of the reference light LR incident on the corner cube and the optical path of the reference light LR emitted from the corner cube are parallel.

The reference light LR that has traveled through the optical path length changing unit 114 passes through the dispersion compensation member 113 and the optical path length correction member 112, is converted from the parallel light flux to the convergent light flux by a collimator 116, and enters an optical fiber 117. The reference light LR that has entered the optical fiber 117 is guided to a polarization controller 118, and the polarization state of the reference light LR is adjusted. Then the reference light LR is guided to an attenuator 120 through an optical fiber 119, and the light amount of the reference light LR is adjusted. After that, the reference light LR is guided to a fiber coupler 122 through an optical fiber 121.

Meanwhile, the measurement light LS generated by the fiber coupler 105 is guided through the optical fiber 127, and is made into the parallel light flux by the collimator lens unit 140. The measurement light LS which has been made into the parallel light flux is deflected one-dimensionally or two-dimensionally by an optical scanner 150.

The collimator lens unit 140 includes a collimator lens. The collimator lens is disposed on an optical axis of the interference optical system included in the OCT optical system 100. The collimator lens converts a light flux of the measurement light emitted from the end of an optical fiber into a parallel light flux. Here, the optical fiber is connected to the OCT optical system 100 and guides the measurement light LS to the end. The end of the optical fiber is arranged at the fundus conjugate position P, for example.

The optical scanner 150 (deflection surface) can be arranged at the pupil conjugate position Q. In case of deflecting in a one-dimensionally manner, the optical scanner 150 includes a galvano scanner that deflects the measurement light LS within a predetermined deflection angle range with reference to a predetermined deflection direction. In case of deflecting in a two-dimensionally manner, the optical scanner 150 includes a first galvano scanner and a second galvano scanner. The first galvano scanner deflects the measurement light LS so as to move the irradiated position in a horizontal direction (for example, x direction) orthogonal to an optical axis of the OCT optical system 100. The second galvano scanner deflects the measurement light LS deflected by the first galvano scanner so as to move the irradiated position in a vertical direction (for example, y direction) orthogonal to the optical axis of the OCT optical system 100. Examples of scan mode for moving the irradiated position of the measurement light LS using the optical scanner 150 include a horizontal scan, a vertical scan, a cross scan, a radial scan, a circle scan, a concentric scan, and a helical (spiral) scan.

The measurement light LS deflected by the optical scanner 150 passes through the focusing lens 151, is reflected by the dichroic mirror 90, passes through the hole in the hole mirror 30, is guided to the reflective surface of the first ellipsoidal mirror 40, and is guided to the subject's eye E along the same path as the illumination light from the slit projection optical system 10. The focusing lens 151 is movable along the optical path of the measurement light LS (optical axis of the OCT optical system 100). The focusing lens 151 is moved along the optical path of the measurement light LS by a movement mechanism (not shown), under the control from the controller described below.

The measurement light LS reflected on the reflective surface of the second ellipsoidal mirror 50 enters the eye of the subject's eye E at the second focal point F4 (subject's eye position) through the pupil. The measurement light LS is scattered (and reflected) at various depth positions of the subject's eye E. The returning light of the measurement light LS including such backscattered light advances through the same path as the outward path in the opposite direction and is guided to the fiber coupler 105, and then reaches the fiber coupler 122 through the optical fiber 128.

The fiber coupler 122 combines (interferes) the measurement light LS incident through the optical fiber 128 and the reference light LR incident through the optical fiber 121 to generate interference light. The fiber coupler 122 generates a pair of interference light LC by splitting the interference light generated from the measurement light LS and the reference light LR at a predetermined splitting ratio (for example, 1:1). The pair of the interference light LC emitted from the fiber coupler 122 is guided to the detector 125 through the optical fibers 123 and 124, respectively.

The detector 125 is, for example, a balanced photodiode that includes a pair of photodetectors for respectively detecting the pair of interference light LC and outputs the difference between the pair of detection results obtained by the pair of photodetectors. The detector 125 sends the detection result (i.e., interference signal) to the DAQ (Data Acquisition System) 130. A clock KC is supplied from the OCT light source 101 to the DAQ 130. The clock KC is generated in the OCT light source 101 in synchronization with the output timing of each wavelength sweeping (scanning) within a predetermined wavelength range performed by the wavelength sweeping type light source. For example, the OCT light source 101 optically delays one of the two pieces of branched light obtained by branching the light L0 of each output wavelength, and then generates the clock KC based on the result of the detection of the combined light of the two pieces of branched light. The DAQ 130 performs sampling of the detection result obtained by the detector 125 based on the clock KC. The DAQ 130 sends the sampled detection result(s) obtained by the detector 125 to the image forming unit 70a, the data processor 75a, and the like. The image forming unit 70a (or data processor 75a) applies Fourier transform and the like to the spectral distribution based on the detection result(s) obtained by the detector 125, for example, with respect to a series of wavelength scans (for each A-line) to form the reflection intensity profile in each A-line. In addition, the image forming unit 70a forms image data by applying imaging processing to the reflection intensity profiles of the each A-line.

It should be noted that the difference between the optical path length of the measurement light and the optical path length of the reference light is changed by changing the optical path length of the reference light, in FIG. 5. However, the configuration according to the embodiments is not limited to this. For example, by changing the optical path length of the measurement light, the difference between the optical path length of the measurement light and the optical path length of the reference light may be configured to be changed.

Figure 6:
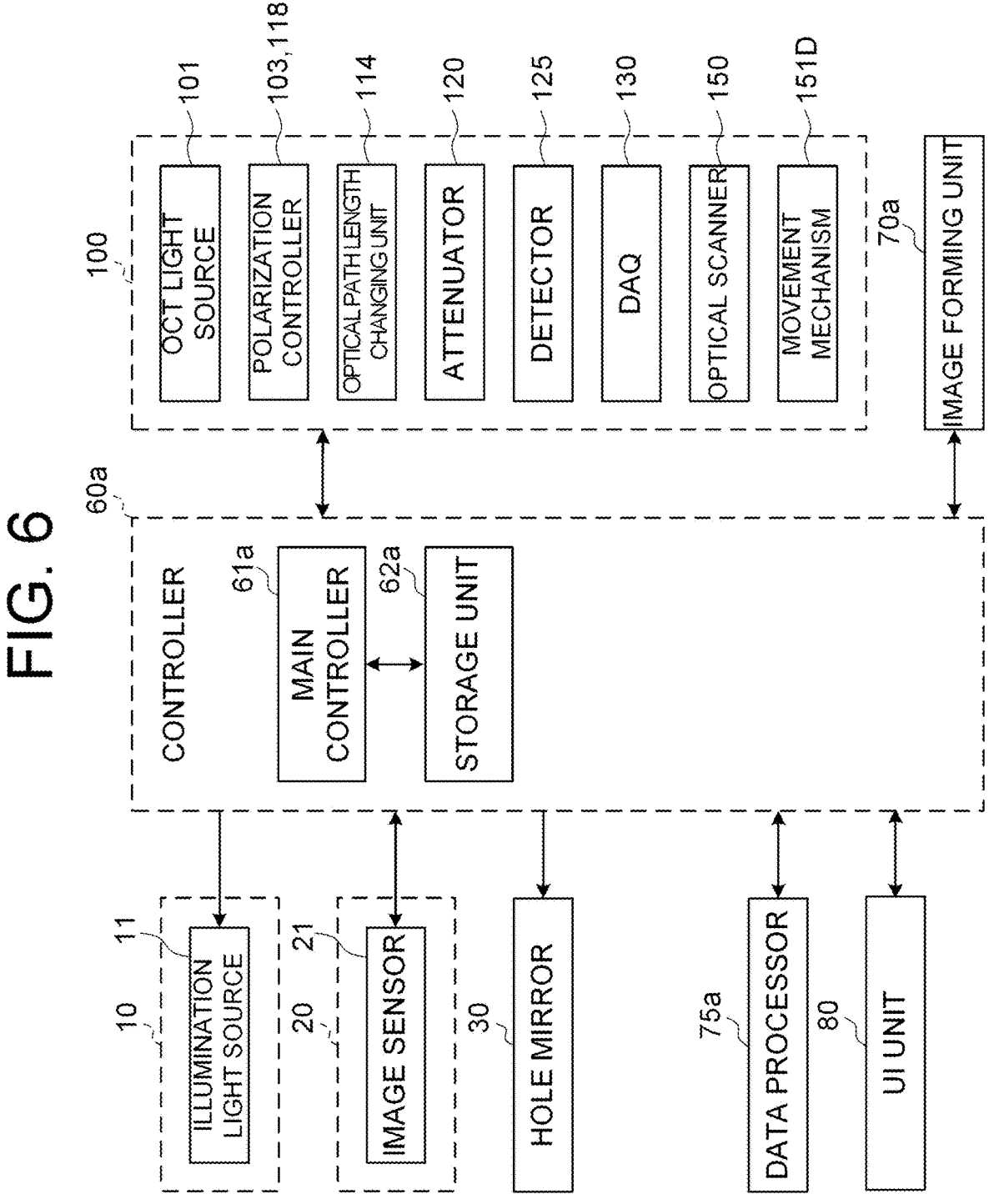
FIG. 6 is a schematic diagram illustrating an example of a configuration of a processing system of the fundus observation apparatus according to the second embodiment.

FIG. 6 shows an example of a configuration of a processing system of the fundus observation apparatus 1a according to the second embodiment. In FIG. 6, like reference numerals designate like parts as in FIG. 2, FIG. 4, or FIG. 5. The same description may not be repeated.

The configuration of the processing system of the fundus observation apparatus 1a differs from that of the processing system of the fundus observation apparatus 1 in that a controller 60a provided instead of the controller 60, that the image forming unit 70a is provided instead of the image forming unit 70, and that the data processor 75a and the OCT optical system 100 are added.

The controller 60a includes a main controller 61a and a storage unit 62a, and in addition to the controls that can be performed by the controller 60, the controller 60a control for the image forming unit 70a, the data processor 75a, and the OCT optical system 100. The functions of the main controller 61a are realized by a processor, for example, in the same way as the main controller 61. The storage unit 62a stores, in advance, computer programs for controlling the fundus observation apparatus 1a, in the same way as the storage unit 62. Examples of the computer programs include an illumination light source control program, an image sensor control program, a hole mirror control program, an image forming program, a program for data processing, a program for controlling OCT optical system, a program for user interface. The main controller 61a operates according to the computer programs, and thereby the controller 60a performs the control processing.

The main controller 61a controls each of the slit projection optical system 10, the a slit light receiving optical system 20, the hole mirror 30, the image forming unit 70a, the data processor 75a, the OCT optical system 100, and the UI unit 80.

Examples of the control for the OCT optical system 100 include control for the OCT light source 101, operation control for polarization controllers 103 and 118, movement control for an optical path length changing unit 114, operation control for an attenuator 120, control for the detector 125, control for the DAQ 130, control for the optical scanner 150, and control for a movement mechanism 151D.

Examples of the control for the OCT light source 101 include turning the light source on and off, adjustment of the light amount, adjustment of an aperture, and the like. Examples of the control for the detector 125 include adjustment of exposure of a detecting element, adjustment of gain of a detecting element, adjustment of detecting rate of a detecting element, and the like. Examples of the control for the optical scanner 150 include control of the scan position, the scan range, and scan speed by the optical scanner 150.

The movement mechanism 151D moves the focusing lens 151 in the optical axis direction of the OCT optical system 100. The main controller 61a can control the movement mechanism 151D to move the focusing lens 151 in the optical axis direction of the OCT optical system 100 and to change the focusing position of the measurement light. The focusing position of the measurement light LS corresponds to the depth position (z position) of the beam waist of the measurement light LS.

Examples of the control for the image forming unit 70a include control of forming OCT images based on the detection result(s) of the interference light obtained by the OCT optical system 100, in addition to the image forming control that forms images of the subject's eye E from the light receiving result(s) obtained using the image sensor 21.

Examples of the data processor 75a include control of image processing for the images formed by the image forming unit 70a and a control of analysis processing for images.

The image forming unit 70a can form the light receiving image (fundus image) corresponding to the arbitrary opening range based on the light receiving result(s) read out from the image sensor 21, in the same way as the image forming unit 70. The image forming unit 70a can sequentially form light receiving light images corresponding to the opening ranges and form an image of the subject's eye E from a plurality of formed light receiving images.

Further, the image forming unit 70a forms image data of the OCT image (tomographic image) based on the detection signals input from the DAQ 130 (detector 125) and pixel position signals input from the controller 60a. Examples of the OCT image formed by the image forming unit 70a include an A-scan image and a B-scan image. The B-scan image is formed by arranging the A-scan images in the B-scan direction. As with the conventional swept source OCT, the image formation process includes noise removal (noise reduction), filtering, dispersion compensation, fast Fourier transform (FFT), and the like. In the case of employing an OCT apparatus of another type, the image forming unit 70a performs known processing according to the type employed. The various images (the various image data) formed by the image forming unit 70a are stored in the storage unit 62a, for example.

The data processor 75a processes images formed based on the light receiving result(s) obtained by the slit light receiving optical system 20 or data acquired by performing OCT measurement on the subject's eye E. The data processor 75a can perform various kinds of image processing and various kinds of analysis processing on the image formed by the image forming unit 70a. For example, the data processor 75a performs various types of image correction processing such as brightness correction.

The data processor 75a performs known image processing such as interpolation processing for interpolating pixels between the OCT images to form image data of the three-dimensional image of the fundus Ef. It should be noted that the image data of the three-dimensional image means image data in which the positions of pixels are defined in a three-dimensional coordinate system. Examples of the image data of the three-dimensional image include image data defined by voxels three-dimensionally arranged. Such image data is referred to as volume data or voxel data. In case of displaying an image based on volume data, the data processor 75a performs image rendering processing (e.g., volume rendering, maximum intensity projection (MIP)) on the volume data to form image data of a pseudo three-dimensional image taken from a specific view direction. The pseudo three-dimensional image is displayed on a display device included in the UI unit 80.

The three-dimensional image data may be stack data of a plurality of tomographic images. The stack data is image data formed by three-dimensionally arranging tomographic images along a plurality of scan lines based on positional relationship of the scan lines. That is, the stack data is image data obtained by representing tomographic images, which are originally defined in their respective two-dimensional coordinate systems, by a single three-dimensional coordinate system. That is, the stack data is image data formed by embedding tomographic images into a single three-dimensional space.

The data processor 75a can form a B-mode image (longitudinal cross-sectional image, axial cross-sectional image) in an arbitrary cross section, a C-mode image (transverse section image, horizontal cross-sectional image) in an arbitrary cross section, a projection image, a shadowgram, etc., by performing various renderings on the acquired three-dimensional data set (volume data, stack data, etc.). An image in an arbitrary cross section such as a B-mode image or a C-mode image is formed by selecting pixels (voxels) on a designated cross section from the three-dimensional data set. The projection image is formed by projecting the three-dimensional data set in a predetermined direction (z direction, depth direction, axial direction). The shadowgram is formed by projecting a part of the three-dimensional data set (for example, partial data corresponding to a specific layer) in a predetermined direction. An image having a viewpoint on the front side of the subject's eye, such as the C-mode image, the projection image, and the shadowgram, is called a front image (en-face image).

The data processor 75a can build (form) the B-mode image or the front image (blood vessel emphasized image, angiogram) in which retinal blood vessels and choroidal blood vessels are emphasized (highlighted), based on data (for example, B-scan image data) acquired in time series by OCT. For example, the OCT data in time series can be acquired by repeatedly scanning substantially the same site of the subject's eye E.

In some embodiments, the data processor 75a compares the B-scan images in time series acquired by B-scan for substantially the same site, converts the pixel value of a change portion of the signal intensity into a pixel value corresponding to the change portion, and builds the emphasized image in which the change portion is emphasized. Further, the data processor 75a forms an OCTA image by extracting information of a predetermined thickness at a desired site from a plurality of built emphasized images and building as an en-face image.

An image (for example, a three-dimensional image, a B-mode image, a C-mode image, a projection image, a shadowgram, and an OCTA image) generated by the data processor 75a is also included in the OCT image.

Further, the data processor 75a performs predetermined analysis processing on the image formed based on the light receiving result(s) obtained by the slit light receiving optical system 20, the detection result of the interference light acquired by the OCT measurement, or the OCT image formed based on the detection result. Examples of the predetermined analysis processing include specifying (identification) of a predetermined site (tissue, lesion) of the subject's eye E; calculation of a distance, area, angle, ratio, or density between designated sites (distance between layers, interlayer distance); calculation by a designated formula; specifying of the shape of a predetermined site; calculation of these statistics; calculation of distribution of the measured value or the statistics; image processing based on these analysis processing results, and the like. Examples of the predetermined tissue include a blood vessel, an optic disc, a fovea, a macula, and the like. Examples of the predetermined lesion include a leukoma, a hemorrhage, and the like.

The fundus observation apparatus 1a may include a movement mechanism that moves the OCT optical system 100 in a one-dimensional or two-dimensional direction intersecting the optical axis of the OCT optical system 100. In this case, the main controller 61a controls this movement mechanism to move the OCT optical system 100 relative to the dichroic mirror 90 in a one-dimensional or two-dimensional direction intersecting the optical axis of the OCT optical system 100. This allows to move the scan range using the optical scanner 150 in the OCT optical system 100 and to scan the wide-angle scan range (e.g., imaging range) on the fundus Ef.

The slit projection optical system 10 and the slit light receiving optical system 20 are an example of the "fundus observation optical system" according to the embodiments. The dichroic mirror 90 is an example of the "optical path coupling separating member" according to the embodiments.

<Operation>

Next, an example of the operation of the fundus observation apparatus 1a according to the second embodiment will be described.

The fundus observation apparatus 1a can perform OCT measurement using the OCT optical system 100 in parallel with the scan control for the fundus Ef using the illumination light shown in FIG. 3. Hereafter, the control of OCT measurement that can be performed in parallel with the control shown in FIG. 3 will be described.

Figure 7:
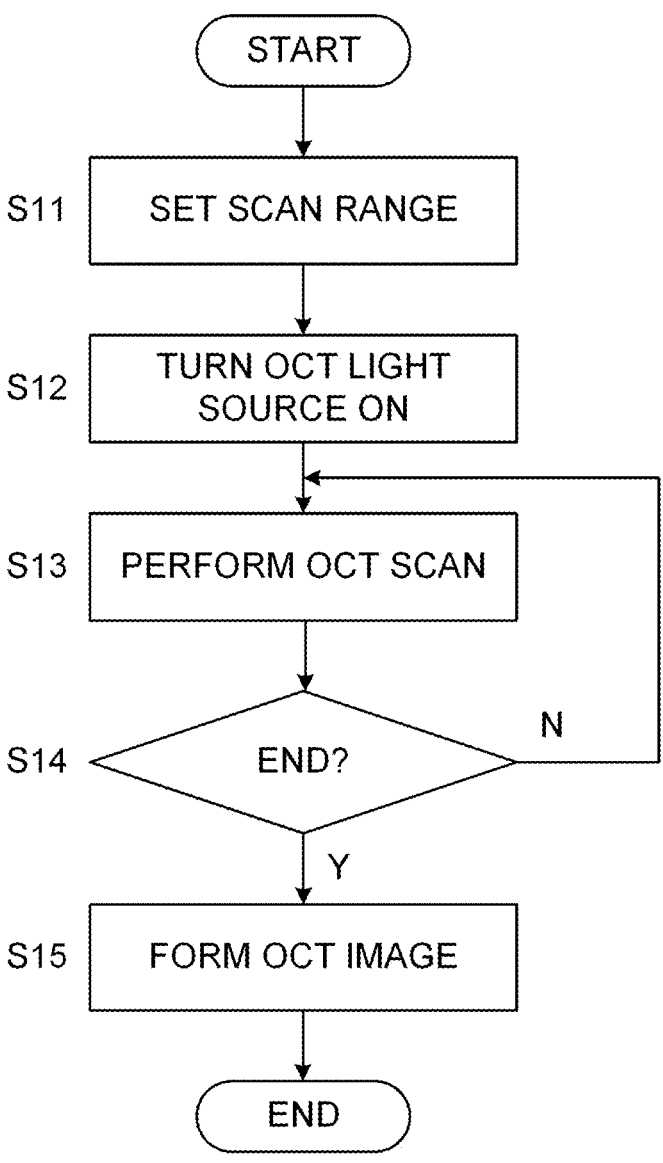
FIG. 7 is a flowchart illustrating an example of an operation of the fundus observation apparatus according to the second embodiment.

FIG. 7 shows an example of the operation of the fundus observation apparatus 1a according to the second embodiment. FIG. 7 represents a flowchart of the example of the operation of the fundus observation apparatus 1a according to the second embodiment. The storage unit 62a stores computer program(s) for realizing the processing shown in FIG. 7. The main controller 61a operates according to the computer programs, and thereby the main controller 101a performs the processing shown in FIG. 7.

It is assumed that the subject's eye E is arranged at a predetermined subject's eye position (the second focal point F4 of the second ellipsoidal mirror 50 in FIG. 1), in FIG. 7.

(S11: Set Scan Range)

First, the main controller 61a sets the scan range of the optical scanner 150. The main controller 61a can set the scan start position, the scan end position, the scan speed (scan frequency), etc. by the optical scanner 150, along with the scan range.

In some embodiments, the user can designate the scan mode or the operation mode by operating the operation device in the UI unit 80. When the scan mode (for example, horizontal scan, vertical scan) is designated by operating the operation device by the user, the main controller 61a analyzes an operation information from the operation device to identify the designated scan mode. When the operation mode is designated by operating the operation device by the user, the main controller 61a analyzes an operation information to identify a scan mode (for example, horizontal scan, vertical scan) designated in advance in the designated operation mode (for example, OCT measurement mode).

(S12: Turn OCT Light Source On)

Subsequently, the main controller 61a controls the OCT light source 101 to turn the OCT light source 101 on. In some embodiments, the main controller 61a performs step S12 in synchronization with the turning on control of the illumination light source 11 in step S1 shown in FIG. 3.

In some embodiments, the main controller 61a performs controls of adjusting focusing and of adjusting polarization. For example, the main controller 61a controls the OCT optical system 100 to perform OCT measurement, after controlling the movement mechanism 151D to move the focusing lens by a predetermined distance. The main controller 61a controls the data processor 75a to determine the focus state of the measurement light LS based on the detection result of the interference light acquired by the OCT measurement. For example, the data processor 75a analyzes the detection results of the interference light acquired by the OCT measurements to calculate predetermined evaluation value(s) relating to the image quality of OCT images and to determine the focus state based on the calculated evaluation value(s). When it is determined that the focus state is not appropriate based on the determination result of the data processor 75a, the main controller 61a controls a movement mechanism 151D again and repeats this until it is determined that the focus state of the measurement light LS is appropriate.

Further, for example, the main controller 61a controls the OCT optical system 100 to perform OCT measurement after controlling at least one of the polarization controller 103 or the polarization controller 118 to change the polarization state of at least one of the light L0 or the measurement light LS by a predetermined amount. And then, the main controller 61a controls the image forming unit 70a to form the OCT image on the basis of the acquired detection result of the interference light. The main controller 61a controls the data processor 75a to determine the image quality of the OCT image acquired by performing the OCT measurement. When it is determined that the polarization state is not appropriate based on the determination result of the data processor 75a, the main controller 61a controls the polarization controllers 103 and 118 again and repeats this until it is determined that the polarization state of the measurement light LS is appropriate.

(S13: Perform OCT Scan)

Subsequently, the main controller 61a controls the optical scanner 150 to deflect the measurement light LS generated based on the light L0 emitted from the OCT light source 101 to scan a predetermined site on the fundus Ef of the subject's eye E with the deflected measurement light LS. The detection result of the interference light acquired by the OCT measurement is sampled by the DAQ 130 and is stored as the interference signal in the storage unit 62a or the like.

(S14: End?)

Subsequently, the main controller 61a determines whether or not to end the OCT scan for the fundus Ef. For example, the main controller 61a can determine whether or not to end the OCT scan for the fundus Ef, by determining whether or not the deflection angle of the deflection surface of the optical scanner 150, which is changed sequentially, is within the predetermined deflection angle range.

When it is determined to end the OCT scan for the fundus Ef (S14: Y), the operation of the fundus observation apparatus 1a proceeds to step S15. When it is determined not to end the OCT scan for the fundus Ef (S14: N), the operation of the fundus observation apparatus 1a proceeds to step S13.

(S15: Form OCT Image)

When it is determined in step S14 to end the OCT scan for the fundus Ef (S14: Y), the main controller 61a controls the image forming unit 70a to form a plurality of A-scan images of the fundus Ef along the B-scan direction, based on the interference signal acquired in step S14. In some embodiments, the main controller 61a controls the data processor 75a to form OCT images such as three-dimensional OCT images, B-mode images, C-mode images, projection images, shadowgrams, and OCTA images.

This ends the operation of the fundus observation apparatus 1a.

Figure 8:
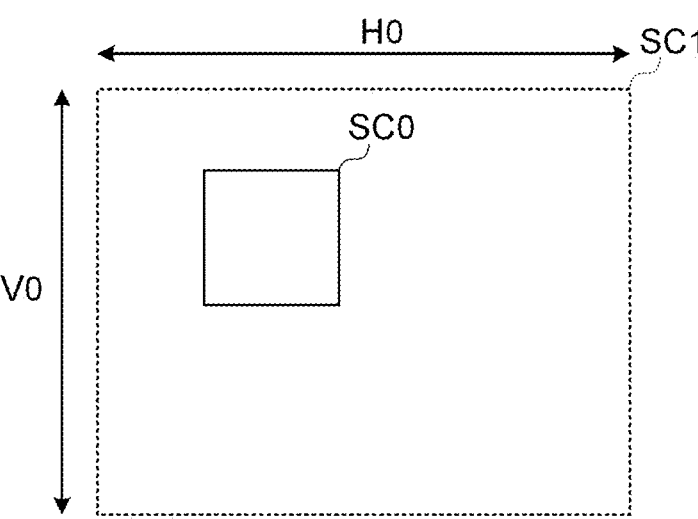
FIG. 8 is a schematic diagram for explaining the operation of the fundus observation apparatus according to the second embodiment.

FIG. 8 shows a diagram explaining the operation of the fundus observation apparatus 1a according to the second embodiment.

As shown in FIG. 8, the scan using the illumination light on the fundus Ef, which is realized by deflecting the illumination light using the hole mirror 30, and the OCT scan on the fundus Ef, which is realized by deflecting the measurement light LS using the optical scanner 150, are performed in parallel. Thereby, when the scan using the illumination light is being performed in a scan range SC1 (horizontal direction H0×vertical direction VO) on the fundus Ef, the OCT scan can be performed on the scan range SC0 at any position within the scan range SC1.

As a result, the OCT measurement (OCT imaging) can be performed on any position of the fundus being observed at a large wide angle by scanning using the illumination light for the scan range SC1.

As described above, according to the second embodiment, in addition to the effects obtained by the first embodiment, by optically coupling the OCT optical system 100 on the transmission side of the hole mirror 30 as the deflecting member (through the hole in the hole mirror), the optical path of the wide-angle illumination light and the optical path of the returning light of the illumination light can be separated at low cost. Further, OCT measurement (OCT imaging) can be performed on any position of the fundus being observed at a large wide angle, without sharing an optical scanner for OCT scanning and an optical scanner for deflection of illumination light.

MODIFICATION EXAMPLE

First Modification Example

In the first embodiment and the second embodiment, the case where the second ellipsoidal mirror 50 is arranged so that the angle α between the straight line connecting the first focal point F1 and the second focal point F2 of the first ellipsoidal mirror 40 and the straight line connecting the first focal point F3 and the second focal point F4 of the second ellipsoidal mirror 50 is 30 degrees has been described. However, the configuration according to the embodiments is not limited to this. For example, the angle α between the straight line connecting the first focal point F1 and the second focal point F2 of the first ellipsoidal mirror 40 and the straight line connecting the first focal point F3 and the second focal point F4 of the second ellipsoidal mirror 50 may be an approximate 0 degree.

Figure 9:
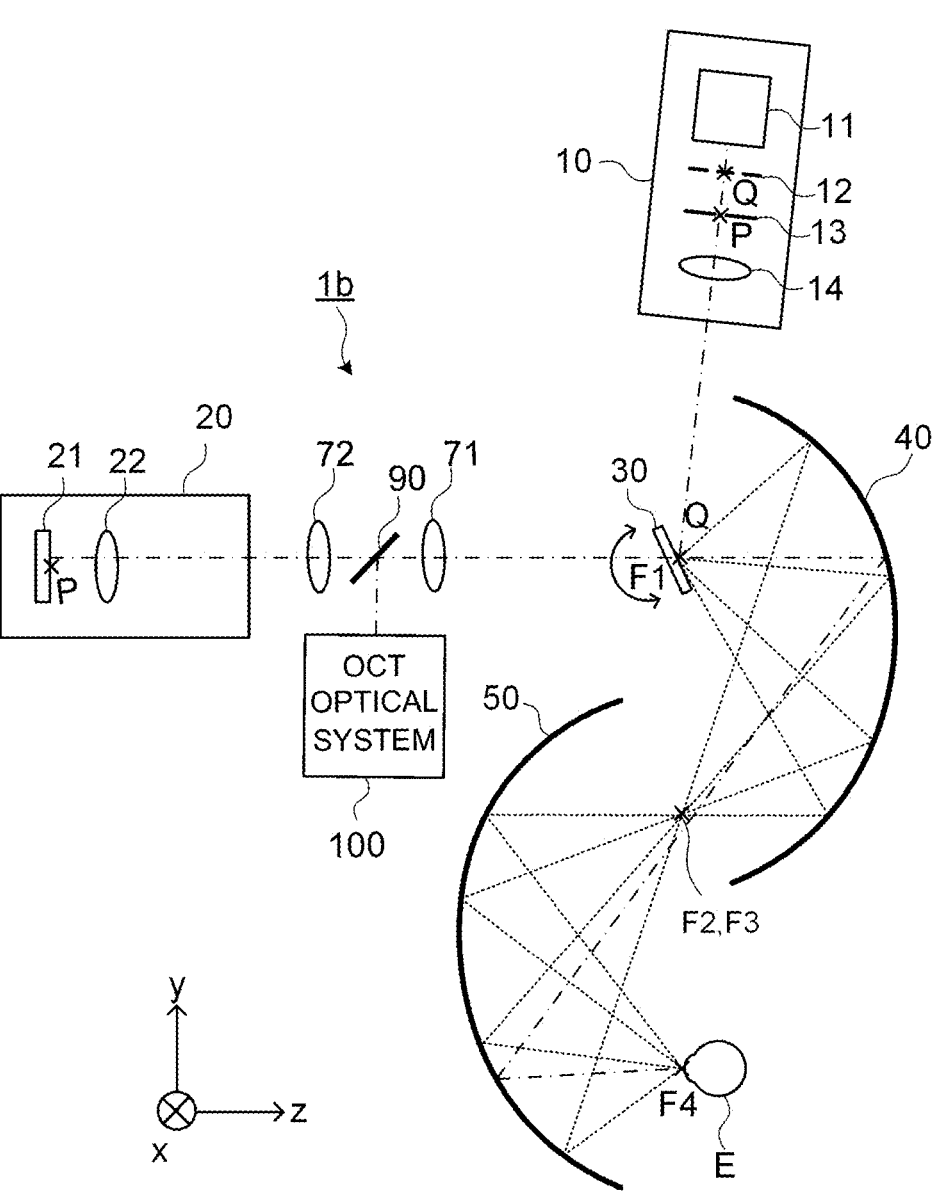
FIG. 9 is a schematic diagram illustrating an example of a configuration of an optical system of the fundus observation apparatus according to a first modification example of the embodiments.

FIG. 9 shows an example of a configuration of an optical system of the fundus observation apparatus according to a first modification example of the embodiments. In FIG. 9, like reference numerals designate like parts as in FIG. 4. The same description may not be repeated.

The difference between the configuration of the optical system of the fundus observation apparatus 1b according to the first modification example of the embodiments and the configuration of the optical system of the fundus observation apparatus 1a according to the second embodiment is the arrangement of the second ellipsoidal mirror 50 relative to the first ellipsoidal mirror 40. In the fundus observation apparatus 1b, the second ellipsoidal mirror 50 is arranged so that the angle α between the straight line connecting the first focal point F1 and the second focal point F2 of the first ellipsoidal mirror 40 and the straight line connecting the first focal point F3 and the second focal point F4 of the second ellipsoidal mirror 50 is 0.2 degrees (approximate 0 degree).

It should be noted that the fundus observation apparatus 1b is provided with the OCT optical system 100, in FIG. 9. However, the fundus observation apparatus 1b may have a configuration in which the OCT optical system 100 is omitted, in the same way as in FIG. 1.

Depending on the angle α described above, the symmetry of the observation range for the subject's eye E changes along with a range of wide angle. According to the first modification example, the fundus Ef can be observed in a wide-angle range that is symmetrical to the subject's eye, compared to the second embodiment.

Second Modification Example

In the first embodiment, the case where the illumination light is deflected using the hole mirror 30 has been described. However, the configuration of the embodiments is not limited thereto. In the first embodiment, for example, a reflective mirror may be placed at the first focal point F1 of the first ellipsoidal mirror 40 and the hole mirror may be placed at a position substantially conjugate optically to the pupil of the subject's eye E.

Figure 10:
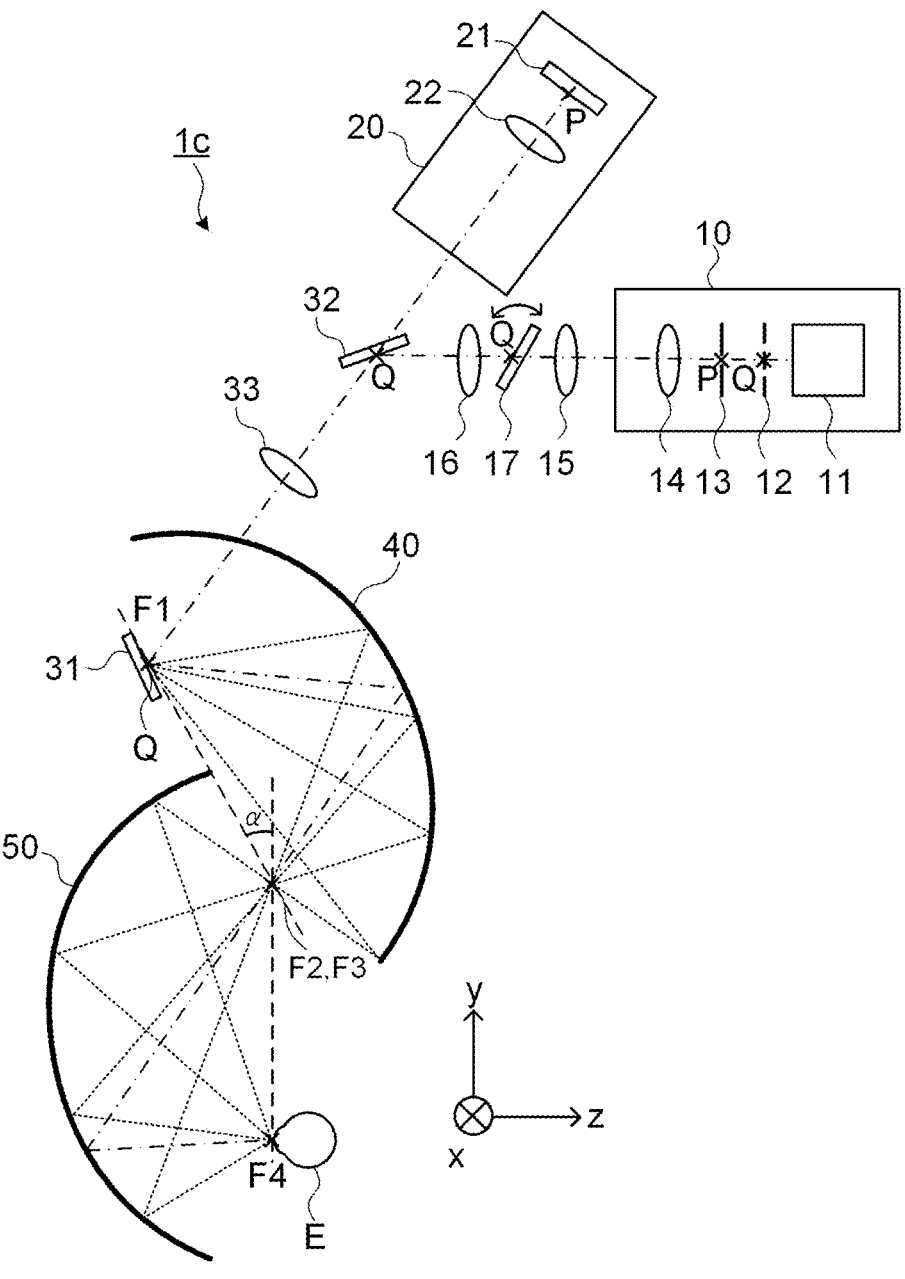
FIG. 10 is a schematic diagram illustrating an example of a configuration of an optical system of the fundus observation apparatus according to a second modification example of the embodiments.

FIG. 10 shows an example of a configuration of an optical system of the fundus observation apparatus according to a second modification example of the embodiments. In FIG. 10, like reference numerals designate like parts as in FIG. 1. The same description may not be repeated.

The configuration of the optical system of the fundus observation apparatus 1c according to the second modification example differs from that of the optical system of the fundus observation apparatus 1 according to the first embodiment in that a reflective mirror 31 is disposed at the first focal point F1 of the first ellipsoidal mirror 40 instead of the hole mirror 30, that the hole mirror 32 is disposed at the pupil conjugate position Q away from the first focal point F1, that an optical scanner 17 is disposed between the hole mirror 32 and the slit projection optical system 10, and that relay lenses 33, 15, and 16 for relaying the pupil conjugate position Q are added.

The orientation of the deflection surface of the reflective mirror 31 is fixed. The relay lens 33 is arranged between the reflective mirror 31 and the hole mirror 32. The hole mirror 32 separates or couples the optical path of the slit projection optical system 10 and the optical path of the slit light receiving optical system 20. The orientation of the deflection surface of the hole mirror 32 is fixed. The relay lens 16, the optical scanner 17, and the relay lens 15 are arranged between the hole mirror 32 and the slit projection optical system 10. The optical scanner 17 is a uniaxial scanner that performs deflection operation of the illumination light in the same way as the hole mirror 30.

In this case, the illumination light from the slit projection optical system 10 passes through the relay lens 15, and is deflected by the optical scanner 17. The illumination light deflected by the optical scanner 17 passes through the relay lens 16, and is deflected on a peripheral region of the hole formed in the hole mirror 32 to be guided to the relay lens 33. The illumination light that has been guided to the relay lens 33 is reflected by the reflective mirror 31 and is guided to the reflective surface of the first ellipsoidal mirror 40. The returning light of the illumination light from the fundus Ef of the subject's eye E is deflected by the reflective mirror 31, passes through the relay lens 33, passes through the hole of the hole mirror 32, and is guided to the slit light receiving optical system 20.

It should be noted that the fundus observation apparatus 1c may have a configuration in which the reflective mirror 31 is omitted in the configuration shown in FIG. 10. In this case, the fundus observation apparatus 1c is configured so that the illumination light passing through the relay lens 33 is directly guided to the reflective surface of the first ellipsoidal mirror 40 and the returning light of the illumination light reflected by the reflective surface of the first ellipsoidal mirror 40 is directly guided to the relay lens 33.

According to the second modification example, compared to the first embodiment, the degree of freedom in the arrangement of the slit projection optical system 10 and the slit light receiving optical system 20 can be improved by relaying the pupil conjugate position Q, even if there is no room for an optical system in the vicinity of the first focal point F1 of the first ellipsoidal mirror 40.

Third Modification Example

In the second embodiments, the case where the illumination light is deflected using the hole mirror 30. However, the configuration according to the embodiments is not limited thereto. In the second embodiment, as in the second modification example, for example, the reflective mirror may be placed at the first focal point F1 of the first ellipsoidal mirror 40, and the hole mirror may be placed at a position substantially conjugate optically to the pupil of the subject's eye E.

Figure 11:
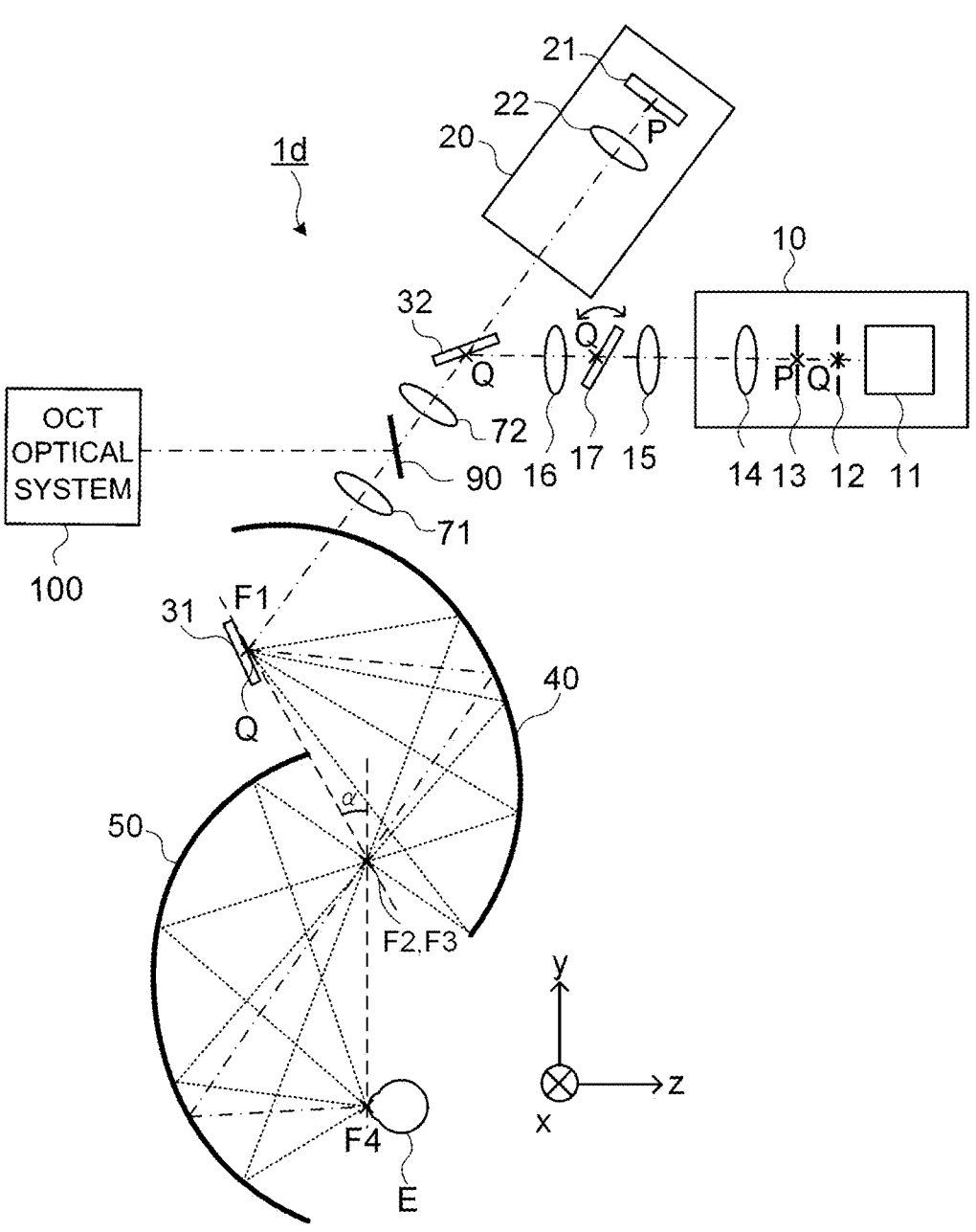
FIG. 11 is a schematic diagram illustrating an example of a configuration of an optical system of the fundus observation apparatus according to a third modification example of the embodiments.

FIG. 11 shows an example of a configuration of an optical system of the fundus observation apparatus according to a third modification example of the embodiments. In FIG. 11, like reference numerals designate like parts as in FIG. 4 or FIG. 10. The same description may not be repeated.

The configuration of the optical system of the fundus observation apparatus 1d according to the third modification example differs that of the optical system of the fundus observation apparatus 1a according to the second embodiment in that the reflective mirror 31 is disposed at the first focal point F1 of the first ellipsoidal mirror 40 instead of the hole mirror 30, that the hole mirror 32 is disposed at the pupil conjugate position Q away from the first focal point F1, that the optical scanner 17 is disposed between the hole mirror 32 and the slit projection optical system 10, and that relay lenses 15 and 16 for relaying the pupil conjugate position Q are added.

The orientation of the deflection surface of the reflective mirror 31 and the orientation of the deflection surface of the hole mirror 32 are fixed, in the same way as in the second modification example. The pupil conjugate position Q is relayed by relay lenses 71 and 72. The hole mirror 32 separates or couples the optical path of the slit projection optical system 10 and the optical path of the slit light receiving optical system 20. The relay lens 16, the optical scanner 17, and the relay lens 15 are arranged between the hole mirror 32 and the slit projection optical system 10. The optical scanner 17 is a uniaxial scanner that performs deflection operation of the illumination light in the same way as the hole mirror 30.

In this case, the illumination light from the slit projection optical system 10 passes through the relay lens 15, and is deflected by the optical scanner 17. The illumination light deflected by the optical scanner 17 passes through the relay lens 16, and is deflected on the peripheral region of the hole formed in the hole mirror 32, passes through the relay lens 72, the dichroic mirror 90, and the relay lens 71, is reflected by the reflective mirror 31, and is guided to the reflective surface of the first ellipsoidal mirror 40. The returning light of the illumination light from the fundus Ef of the subject's eye E is deflected by the reflective mirror 31, passes through the relay lens 71, the dichroic mirror 90, and the relay lens 72, passes through the hole of the hole mirror 32, and is guided to the slit light receiving optical system 20.

According to the third modification example, compared to the second embodiment, the degree of freedom in the arrangement of the slit projection optical system 10 and the slit light receiving optical system 20 can be improved by relaying the pupil conjugate position Q, even if there is no room for an optical system in the vicinity of the first focal point F1 of the first ellipsoidal mirror 40.

Fourth Modification Example

In the above embodiments or the modification examples thereof, the hole mirror 30 that performs the deflection operation of the illumination light may have the following configuration.

Figure 12A:
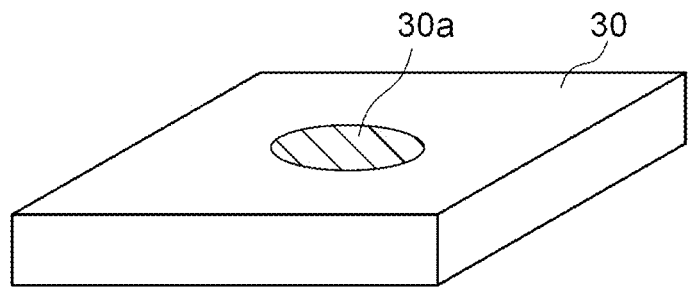
FIG. 12A is a schematic diagram illustrating an example of a configuration of an optical system of the fundus observation apparatus according to a fourth modification example of the embodiments.
Figure 12B:
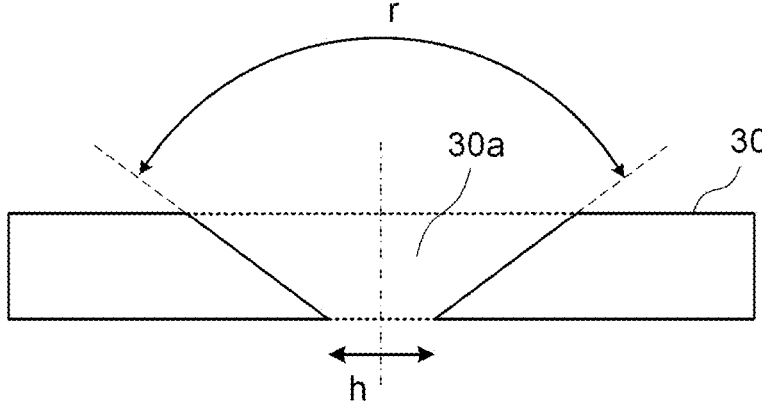
FIG. 12B is a schematic diagram illustrating an example of a configuration of an optical system of the fundus observation apparatus according to the fourth modification example of the embodiments.

FIG. 12A and FIG. 12B schematically show a configuration of the hole mirror 30 according to a fourth modification example of the embodiments. FIG. 12A schematically represents an overview of the configuration of the hole mirror 30 according to the present modification example. FIG. 12B schematically represents the cross-sectional shape when cut in the cutting plane passing through the hole of the hole mirror 30 in FIG. 12A.

As shown in FIG. 12A, a hole 30a processed into a tapered shape is formed in the hole mirror 30. For example, as shown in FIG. 12B, the tapered hole 30a is formed so that the diameter widens in an angle range "r" from an opening of diameter "h" centered on the optical axis. For example, the diameter "h" is 3 to 4 mm and the angle range "r" is 120 degrees.

For example, the surface with the larger diameter of the hole 30a is positioned so as to face the slit light receiving optical system 20. In other words, the hole mirror 30 is arranged so that the opening on the surface of the side of the slit light receiving optical system 20, which receives the returning light of the illumination light, is wider than the opening on the deflection surface side of the illumination light. That is, the tapered hole 30a is formed in the center part of the hole mirror 30 so that an opening size on the light receiving side of the returning light of the illumination light becomes larger. Thereby, even when the hole mirror 30 is tilted with respect to the optical axis, the occurrence of vignetting of the light flux of the returning light on the light receiving side can be suppressed.

Fifth Modification Example

In the embodiments described above or the modification examples thereof, the hole mirror 30 (or hole mirror 32) is not limited to the configuration according to the fourth modification example.

Figure 13A:
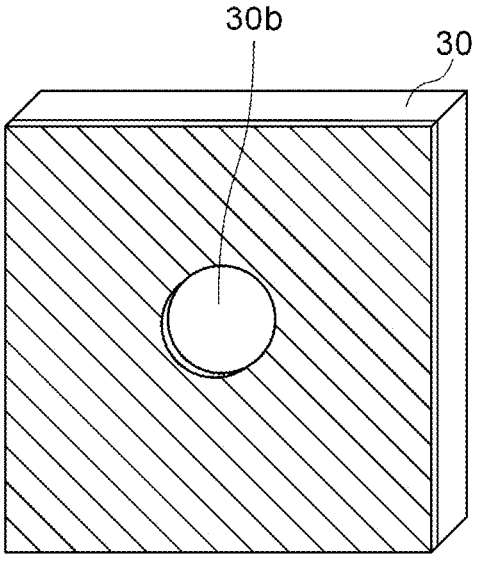
FIG. 13A is a schematic diagram illustrating an example of a configuration of an optical system of the fundus observation apparatus according to a fifth modification example of the embodiments.
Figure 13B:
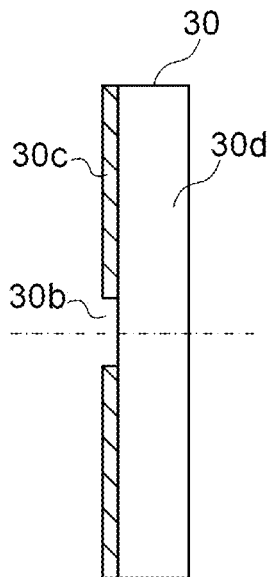
FIG. 13B is a schematic diagram illustrating an example of a configuration of an optical system of the fundus observation apparatus according to the fifth modification example of the embodiments.

FIG. 13A and FIG. 13B schematically show a configuration of the hole mirror 30 according to a fifth modification example of the embodiments. FIG. 13A schematically represents an overview of the configuration of the hole mirror 30 according to the present modification example. FIG. 13B schematically represents the cross-sectional shape when cut in the cutting plane passing through the hole of the hole mirror 30 in FIG. 13A.

As shown in FIG. 13B, the hole mirror 30 includes a plane parallel plate 30d made from a transmissive member through which at least the returning light of the illumination light can be transmitted, and a reflective film 30c provided on the surface of the plane parallel plate 30d. An opening 30b is formed in the center of the reflective film 30c, through which the optical axis passes. For example, the reflective film 30c is formed by evaporating a metal film or a dielectric multi-layer film onto the surface of the plane parallel plate 30d.

For example, the surface on which the reflective film 30c is not provided is positioned so as to face the slit light receiving optical system 20. In other words, the hole mirror 30 is arranged so that the illumination light is reflected on the reflective film 30c provided on the surface of the plane parallel plate 30d without being transmitted through the transmitting member.

Sixth Modification Example

The configuration of the fundus observation apparatus according to the embodiments is not limited to the configuration according to the embodiments or the modification examples thereof described above. For example, three or more aspheric mirrors may be provided instead of the first ellipsoidal mirror 40 and the second ellipsoidal mirror 50. Examples of the aspheric mirror include a paraboloidal mirror, a hyperboloidal mirror, a mirror whose reflecting surface is represented by higher-order polynomials, in addition to the ellipsoidal mirror. In some embodiments, the three or more aspheric mirrors includes a free-form surface mirror.

In the present modification example, two concave mirrors (aspheric mirrors) and a single convex mirror (aspheric mirror) are provided instead of the first ellipsoidal mirror 40 and the second ellipsoidal mirror 50.

In the following, the fundus observation apparatus according a sixth modification example of the embodiments will be described focusing on differences from the fundus observation apparatus 1 according to the first embodiment.

Figure 14:
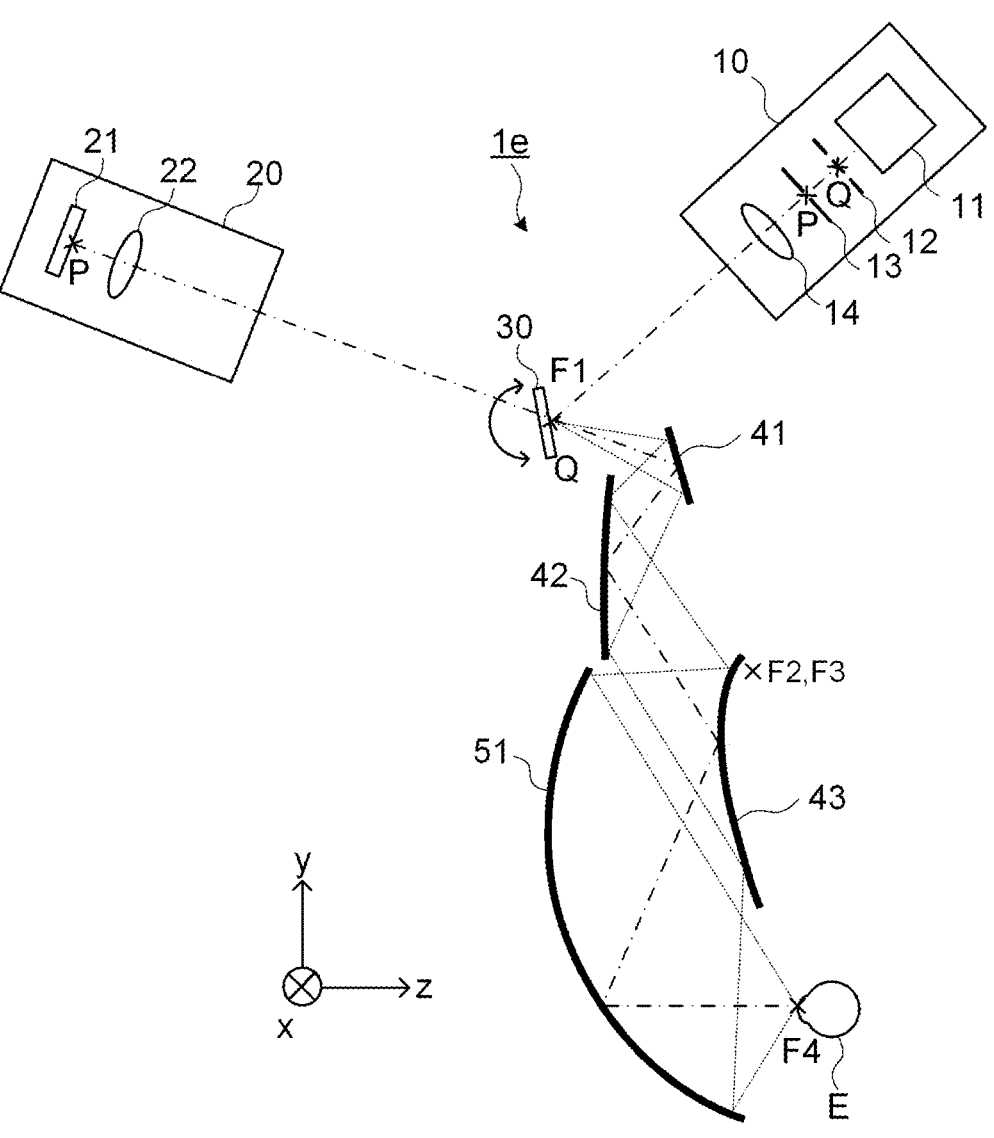
FIG. 14 is a schematic diagram illustrating an example of a configuration of an optical system of the fundus observation apparatus according to a sixth modification example of the embodiments.

FIG. 14 shows an example of a configuration of an optical system of the fundus observation apparatus according to the sixth modification example of the embodiments. In FIG. 14, like reference numerals designate like parts as in FIG. 1. The same description may not be repeated.

The configuration of the optical system of the fundus observation apparatus 1e according to the present modification example differs from that of the optical system of the fundus observation apparatus 1 according to the embodiments in that a reflective mirror 41 as a plane mirror, a hyperboloidal mirror 42 as a concave mirror, a hyperboloidal mirror 43 as a convex mirror, and an ellipsoidal mirror 51 as a concave mirror are provided instead of the first ellipsoidal mirror 40 and the second ellipsoidal mirror 50.

The reflective mirror 41 reflects the illumination light reflected by the hole mirror 30, and guides the illumination light to the hyperboloidal mirror 42. Further, the reflective mirror 41 reflects the returning light of the illumination light reflected on the reflective surface of the hyperboloidal mirror 42, and guides the returning light to the hole mirror 30. In some embodiments, the fundus observation apparatus 1e may have a configuration in which the reflective mirror 41 is omitted.

By deflecting the optical axis using the reflective mirror 41, the size in the depth direction (z direction) of the optical system of the fundus observation apparatus 1e can be reduced.

(Hyperboloidal Mirror 42)

The hyperboloidal mirror 42 has a concave surface-shaped reflective surface. A reflective surface of the hyperboloidal mirror 42 is a hyperboloid. The hyperboloidal mirror 42 is an example of the concave mirror.

One of focal points of the hyperboloidal mirror 42 is the first focal point F1. The hole mirror 30 (deflection surface of the hole mirror 30) is positioned at the first focal point F1 of the hyperboloidal mirror 42 or near the first focal point F1. In some embodiments, the hole mirror 30 is positioned at a position conjugate optically to the first focal point F1 (conjugate position of the first focal point F1) or near the position.

(Hyperboloidal Mirror 43)

The hyperboloidal mirror 43 has a convex-shaped reflective surface. A reflective surface of the hyperboloidal mirror 43 is a hyperboloid. The hyperboloidal mirror 43 is an example of the convex mirror.

One of focal points of the hyperboloidal mirror 43 is the second focal point F2.

(Ellipsoidal Mirror 51)

A reflective surface of the ellipsoidal mirror 51 is an elliptical surface. The ellipsoidal mirror 51 is an example of the concave mirror.

The ellipsoidal mirror 51 has two optically conjugate focal points (first focal point F3, second focal point F4). The ellipsoidal mirror 51 is arranged so that the first focal point F3 substantially coincides with the second focal point F4 of the hyperboloidal mirror 43. In some embodiments, the ellipsoidal mirror 51 is arranged so that the first focal point F3 substantially coincides with a position conjugate optically to the second focal point F2 of the hyperboloidal mirror 43 (conjugate position of the second focal point F2) or near the position. The subject's eye E is arranged at the second focal point F4 of the ellipsoidal mirror 51. In other words, the ellipsoidal mirror 51 is arranged so that the second focal point F4 substantially coincides with the subject's eye position where the subject's eye E is arranged.

In such a configuration, the illumination light deflected by the hole mirror 30 arranged at the first focal point F1 is reflected on the reflective surface of the reflective mirror 41, is reflected on the concave-shaped reflective surface of the hyperboloidal mirror 42, is reflected on the convex-shaped reflective surface of the hyperboloidal mirror 43, is reflected on the reflective surface of the ellipsoidal mirror 51, and is guided to the subject's eye E arranged at the second focal point F4 of the ellipsoidal mirror 51.

The illumination light that has been guided to the subject's eye E enters the eye through the pupil and is irradiated onto the fundus Ef. The returning light of the illumination light reflected on the fundus Ef is emitted outside of the subject's eye E through the pupil, travels in the same path as the outward path in the opposite direction, and is guided to the first focal point F1 of the hyperboloidal mirror 42. The returning light of the illumination light that has been guided to the first focal point F1 passes through the hole formed in the hole mirror 30 (or is transmitted through the hole mirror 30), and is guided to the slit light receiving optical system 20, as described above.

In some embodiments, at least one of the hyperboloidal mirrors 42 and 43 is a paraboloidal mirror. In some embodiments, at least one of the hyperboloidal mirrors 42 and 43, and the ellipsoidal mirror 51 is formed so that the reflective surface is free-form surface.

It should be noted that three or more aspheric mirrors may be provided instead of the first ellipsoidal mirror 40 and the second ellipsoidal mirror 50 in the configuration shown in FIG. 4 or FIG. 9, in the same way as in the present modification example.

Seventh Modification Example

The configuration of the fundus observation apparatus according to the embodiments is not limited to the configuration according to the embodiments or the modification examples thereof described above. For example, in the configuration shown in FIG. 10, three or more aspheric mirrors may be provided instead of the first ellipsoidal mirror 40 and the second ellipsoidal mirror.

In the present modification example, as in the sixth modification example, two concave mirrors (aspheric mirrors) and a single convex mirror (aspheric mirror) are provided instead of the first ellipsoidal mirror 40 and the second ellipsoidal mirror.

In the following, the fundus observation apparatus according a seventh modification example of the embodiments will be described focusing on differences from the fundus observation apparatus 1c according to the second modification example.

Figure 15:
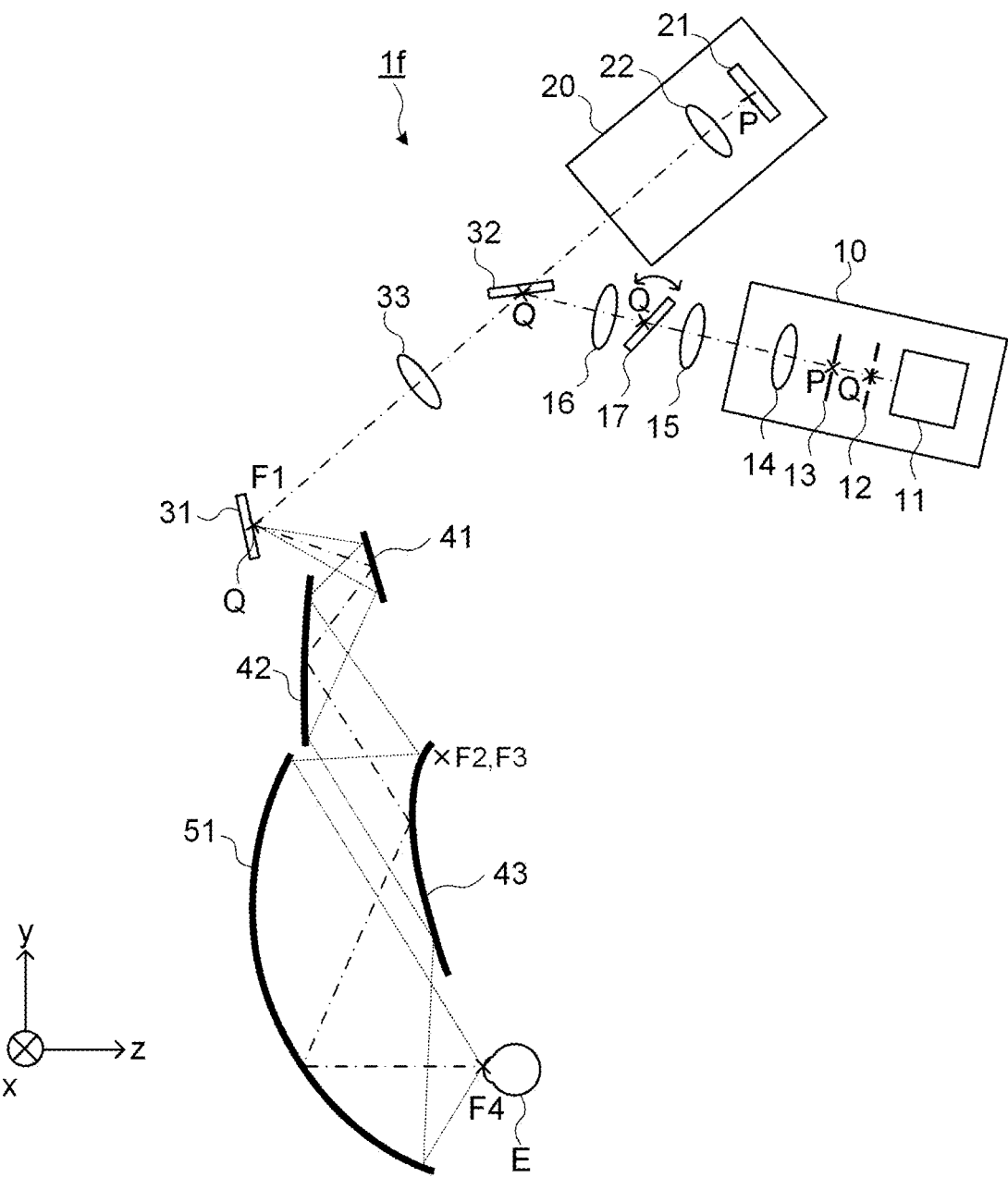
FIG. 15 is a schematic diagram illustrating an example of a configuration of an optical system of the fundus observation apparatus according to a seventh modification example of the embodiments.

FIG. 15 shows an example of a configuration of an optical system of the fundus observation apparatus according to the seventh modification example of the embodiments. In FIG. 15, like reference numerals designate like parts as in FIG. 10 or FIG. 14. The same description may not be repeated.

The configuration of the optical system of the fundus observation apparatus if according to the present modification example differs from that of the optical system of the fundus observation apparatus 1c according to the second modification example in that the reflective mirror 41 as a plane mirror, the hyperboloidal mirror 42 as a concave mirror, the hyperboloidal mirror 43 as a convex mirror, and the ellipsoidal mirror 51 as a concave mirror are provided instead of the first ellipsoidal mirror 40 and the second ellipsoidal mirror 50.

In such a configuration, the illumination light deflected by the reflective mirror 31 arranged at the first focal point F1 is reflected on the reflective surface of the reflective mirror 41, is reflected on the concave-shaped reflective surface of the hyperboloidal mirror 42, is reflected on the convex-shaped reflective surface of the hyperboloidal mirror 43, is reflected on the reflective surface of the ellipsoidal mirror 51, and is guided to the subject's eye E arranged at the second focal point F4 of the ellipsoidal mirror 51.

The illumination light that has been guided to the subject's eye E enters the eye through the pupil and is irradiated onto the fundus Ef. The returning light of the illumination light reflected on the fundus Ef is emitted outside of the subject's eye E through the pupil, travels in the same path as the outward path in the opposite direction, and is guided to the first focal point F1 of the hyperboloidal mirror 42. The returning light of the illumination light that has been guided to the first focal point F1 passes through the hole formed in the hole mirror 30 (or is transmitted through the hole mirror 30), and is guided to the slit light receiving optical system 20, as described above.

In some embodiments, at least one of the hyperboloidal mirrors 42 and 43 is a paraboloidal mirror. In some embodiments, at least one of the hyperboloidal mirrors 42 and 43, and the ellipsoidal mirror 51 is formed so that the reflective surface is free-form surface.

It should be noted that three or more aspheric mirrors may be provided instead of the first ellipsoidal mirror 40 and the second ellipsoidal mirror 50 in the configuration shown in FIG. 11, in the same way as in the present modification example.

Eighth Modification Example

In the embodiments or the modification examples thereof described above, in the fundus observation apparatus, one or more aspherical refractive optical elements may be placed in the optical path of the illumination light and the optical path of the returning light of the illumination light.

The aspherical refractive optical element can correct aberration components inherent in the mirrors whose reflective surfaces are quadric surfaces, such as the ellipsoidal mirror, the hyperboloidal mirror, and the paraboloidal mirror, by providing asymmetric aberration components in a predetermined direction (intersecting direction to the optical axis) for the incident light. In other words, when the aspheric mirror such as the ellipsoidal mirror, the hyperboloidal mirror, and the paraboloidal mirror is configured asymmetrically in a direction orthogonal (broadly speaking, intersecting) to the optical axis (e.g., the optical path of the illumination light or the returning light thereof), the aspherical refractive optical element(s) can correct aberrations corresponding to the amount of deviation from the optical axis, and thus an imaging characteristic based on the incident light can be improved.

Examples of the aspherical refractive optical element include an aspheric lens, such as an anamorphic aspheric lens.

Each of the one or more aspherical refractive optical elements is preferably disposed at the pupil conjugate position Q. This allows to reduce the diameter of the aspherical refractive optical element(s).

In the following, the fundus observation apparatus according an eighth modification example of the embodiments will be described focusing on differences from the fundus observation apparatus 1 according to the first embodiment.

Figure 16A:
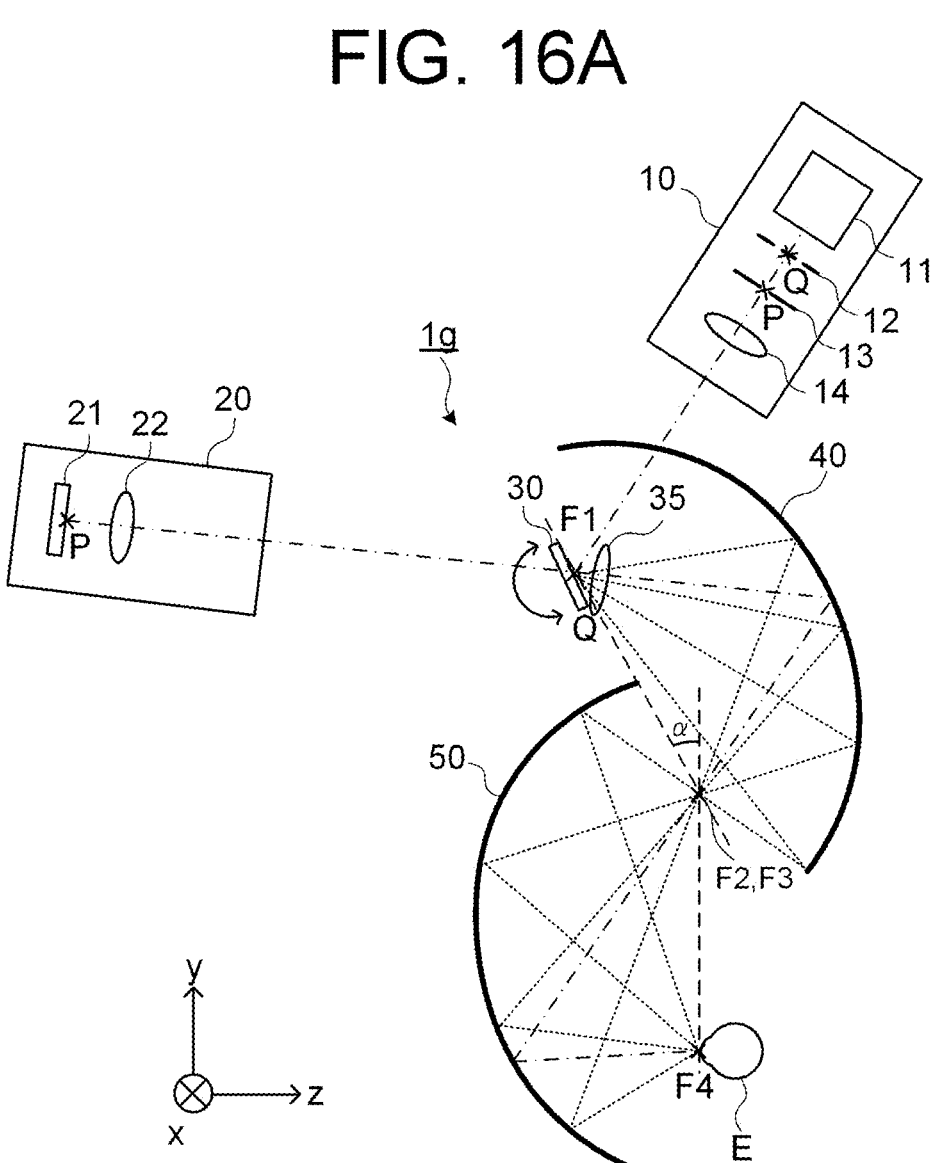
FIG. 16A is a schematic diagram illustrating an example of a configuration of an optical system of the fundus observation apparatus according to an eighth modification example of the embodiments.

FIG. 16A shows an example of a configuration of an optical system of the fundus observation apparatus according to the eighth modification example of the embodiments. In FIG. 16A, like reference numerals designate like parts as in FIG. 1. The same description may not be repeated.

The configuration of the optical system of the fundus observation apparatus 1g according to the present modification example differs from that of the optical system of the fundus observation apparatus 1 according to the embodiments in that an aspherical refractive optical element 35 is disposed between the hole mirror 30 and the first ellipsoidal mirror 40. In other words, the aspherical refractive optical element 35 is disposed on the optical path of the illumination light and the optical path of the returning light of the illumination light.

In the present modification example, when at least one of the first ellipsoidal mirror 40 and the second ellipsoidal mirror 50 is configured asymmetrically in the y direction (first direction) with respect to the optical path (optical axis) of the illumination light or the returning light thereof, the aspherical refractive optical element 35 adds an aberration component asymmetric in the y direction with respect to the incident light. This allows to correct the aberration components of the first ellipsoidal mirror 40 and the second ellipsoidal mirror 50.

Figure 16B:
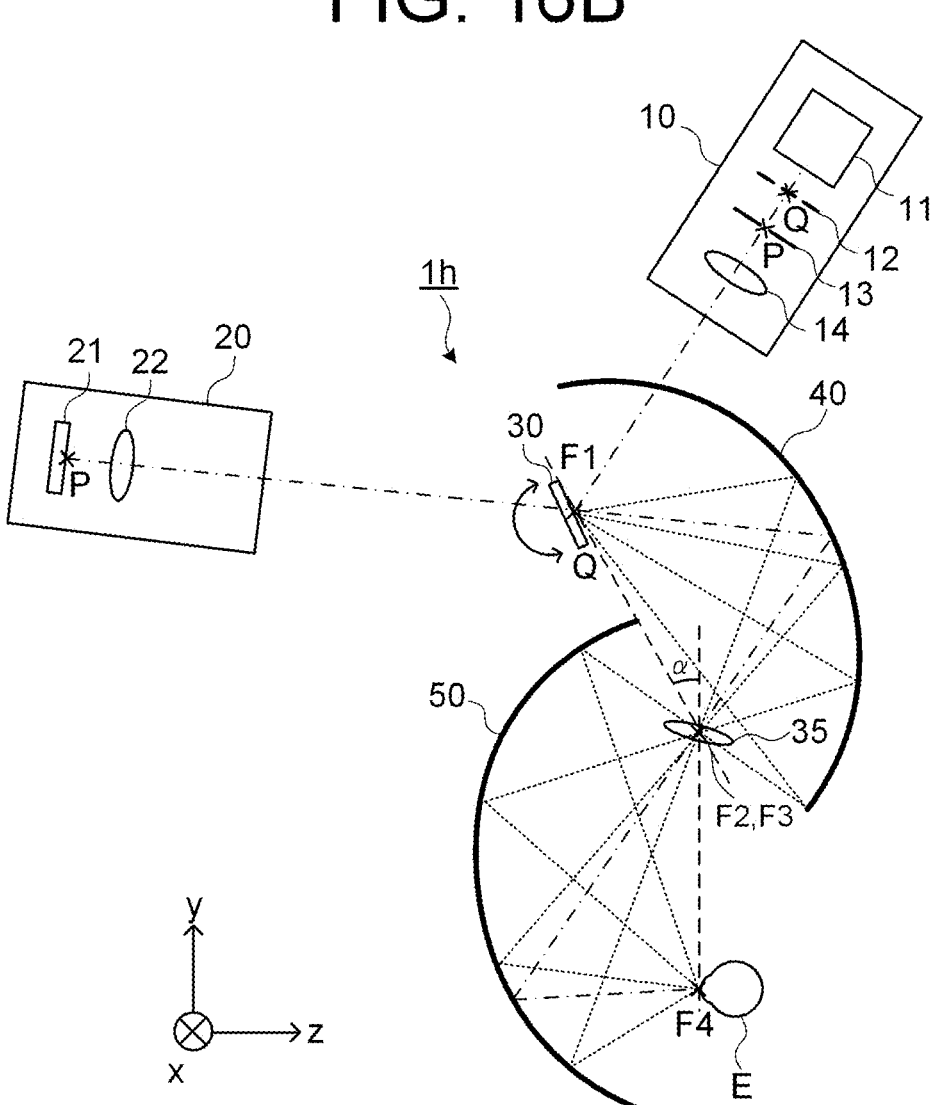
FIG. 16B is a schematic diagram illustrating an example of a configuration of an optical system of the fundus observation apparatus according to the eighth modification example of the embodiments.

FIG. 16B shows an another example of a configuration of an optical system the another of the fundus observation apparatus according to the eighth modification example of the embodiments. In FIG. 16B, like reference numerals designate like parts as in FIG. 1 or FIG. 16A. The same description may not be repeated.

The configuration of the optical system of the fundus observation apparatus 1h according to the present modification example differs from that of the optical system of the fundus observation apparatus 1 according to the embodiments in that the aspherical refractive optical element 35 is disposed between the first ellipsoidal mirror 40 and the second ellipsoidal mirror 50. In other words, the aspherical refractive optical element 35 is disposed on the optical path of the illumination light and the optical path of the returning light of the illumination light.

In the present modification example, when at least one of the first ellipsoidal mirror 40 and the second ellipsoidal mirror 50 is configured asymmetrically in the y direction with respect to the optical path (optical axis) of the illumination light or the returning light thereof, the aspherical refractive optical element 35 adds an aberration component asymmetric in the y direction with respect to the incident light. This allows to correct the aberration components of the first ellipsoidal mirror 40 and the second ellipsoidal mirror 50.

Figure 16C:
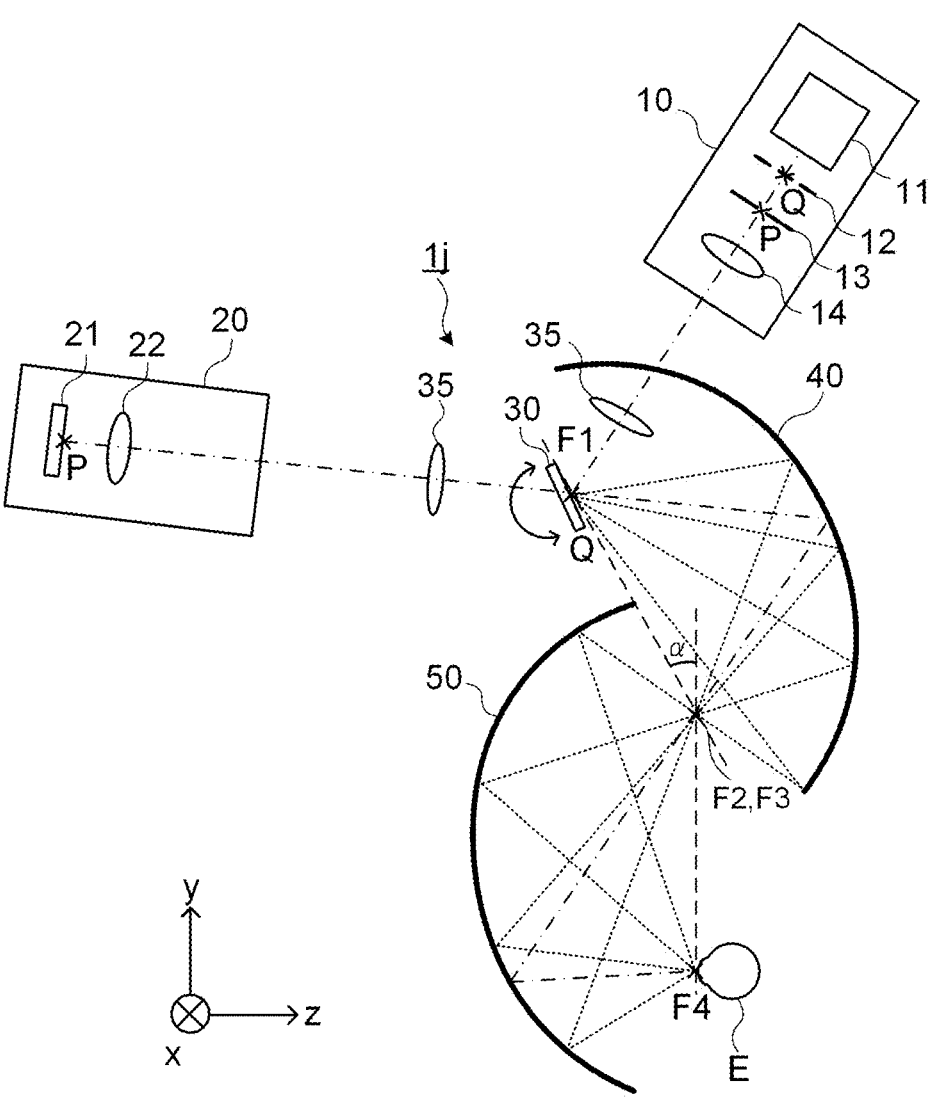
FIG. 16C is a schematic diagram illustrating an example of a configuration of an optical system of the fundus observation apparatus according to the eighth modification example of the embodiments.

FIG. 16C shows a still another example of a configuration of an optical system of the fundus observation apparatus according to the eighth modification example of the embodiments. In FIG. 16C, like reference numerals designate like parts as in FIG. 1 or FIG. 16A. The same description may not be repeated.

The configuration of the optical system of the fundus observation apparatus 1j according to the present modification example differs from that of the optical system of the fundus observation apparatus 1 according to the embodiments in that an aspherical refractive optical element 35 is disposed on the optical path of the illumination light between the slit projection optical system 10 and the hole mirror 30, and that an aspherical refractive optical element 35 is disposed on the optical path of the returning light of the illumination light between the hole mirror 30 and the slit light receiving optical system 20. In other words, the two aspherical refractive optical elements 35 are disposed on the optical path of the illumination light and the optical path of the returning light of the illumination light.

In the present modification example, when at least one of the first ellipsoidal mirror 40 and the second ellipsoidal mirror 50 is configured asymmetrically in the y direction with respect to the optical path (optical axis) of the illumination light or the returning light thereof, each of the aspherical refractive optical elements 35 adds an aberration component asymmetric in the y direction with respect to the incident light. This allows to correct the aberration components of the first ellipsoidal mirror 40 and the second ellipsoidal mirror 50.

It should be noted that in the configuration shown in FIG. 4, FIG. 9, or FIG. 14, one or more aspherical refractive optical elements may be disposed on the optical path of the illumination light and the optical path of the returning light of the illumination light, as in the present modification example. In the configuration shown in FIG. 14, when at least one of the hyperboloidal mirrors 42 and 43, and the ellipsoidal mirror 51 is configured asymmetrically in the y direction with respect to the optical path (optical axis) of the illumination light or the returning light thereof, the aspherical refractive optical element 35 adds an aberration component asymmetric in the y direction with respect to the incident light. This allows to correct the aberration components of the hyperboloidal mirrors 42 and 43, and the ellipsoidal mirror 51.

Further, in the configuration shown in FIG. 4 or FIG. 9, the aspherical refractive optical element 35 may be disposed between the dichroic mirror 90 and the OCT optical system 100. In some embodiments, the aspherical refractive optical element 35 is disposed only between the dichroic mirror 90 and the OCT optical system 100, without the aspherical refractive optical element 35 being disposed on the optical path of the illumination light and the optical path of the returning light of the illumination light.

The case where the aberrations in the y direction are corrected has been described in the present modification example. However, aberrations in the x direction may be corrected. Further, when the aspheric mirror described above is configured to be asymmetric in the x and y directions, the aberrations in the x and y directions may be corrected.

Ninth Modification Example

For example, in the configuration shown in FIG. 10, one or more aspherical refractive optical elements may be disposed on the optical path of the illumination light and the optical path of the returning light of the illumination light, as in the eighth modification example.

In the following, the fundus observation apparatus according a ninth modification example of the embodiments will be described focusing on differences from the fundus observation apparatus 1c according to the second modification example.

Figure 17A:
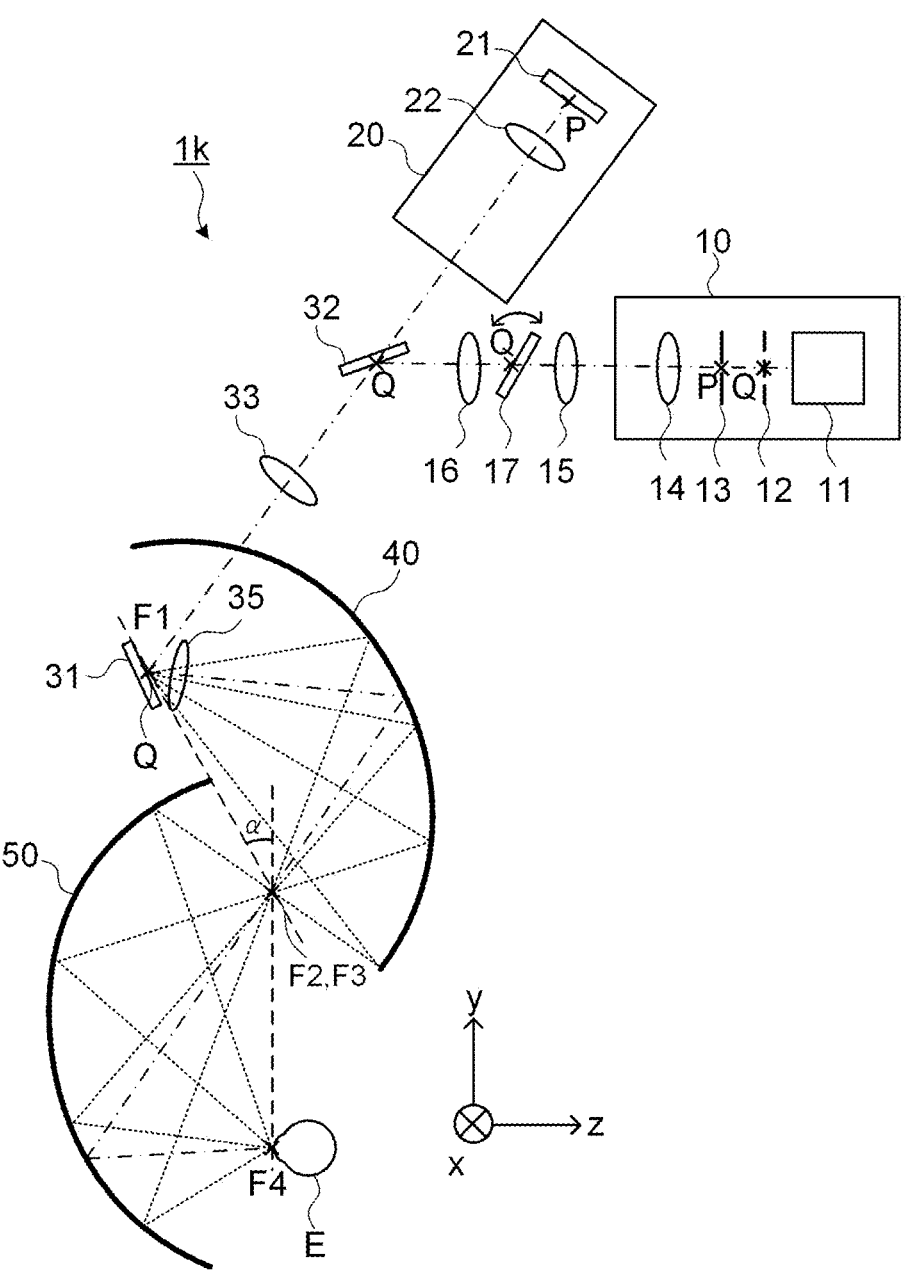
FIG. 17A is a schematic diagram illustrating an example of a configuration of an optical system of the fundus observation apparatus according to a ninth modification example of the embodiments.

FIG. 17A shows an example of a configuration of an optical system of the fundus observation apparatus according to the ninth modification example of the embodiments. In FIG. 17A, like reference numerals designate like parts as in FIG. 10. The same description may not be repeated.

The configuration of the optical system of the fundus observation apparatus 1k according to the present modification example differs from that of the optical system of the fundus observation apparatus 1c according to the second modification example in that the aspherical refractive optical element 35 is disposed between the reflective mirror 31 and the first ellipsoidal mirror 40. In other words, the aspherical refractive optical element 35 is disposed on the optical path of the illumination light and the optical path of the returning light of the illumination light.

In the present modification example, when at least one of the first ellipsoidal mirror 40 and the second ellipsoidal mirror 50 is configured asymmetrically in the y direction with respect to the optical path (optical axis) of the illumination light or the returning light thereof, the aspherical refractive optical element 35 adds an aberration component asymmetric in the y direction with respect to the incident light. This allows to correct the aberration components of the first ellipsoidal mirror 40 and the second ellipsoidal mirror 50.

Figure 17B:
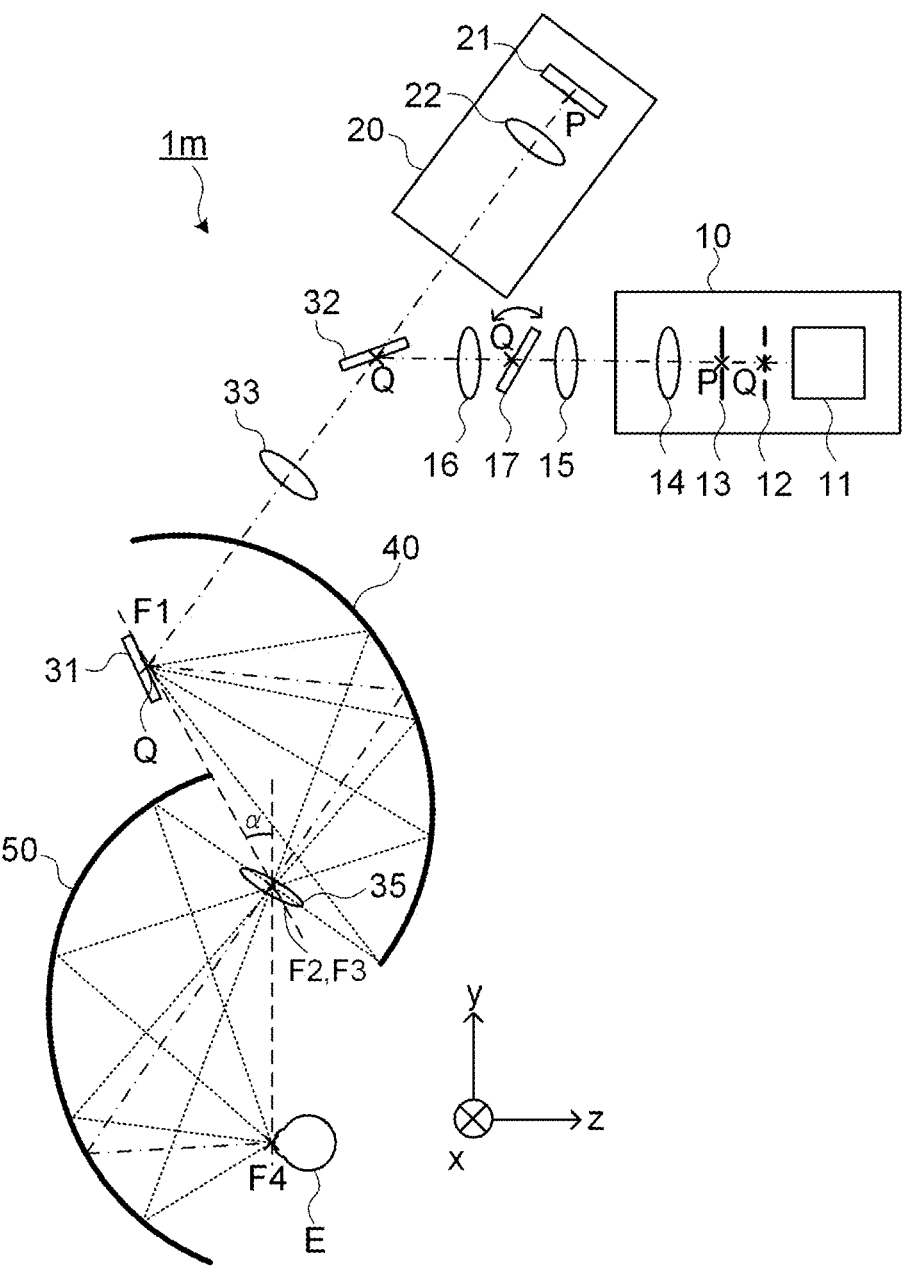
FIG. 17B is a schematic diagram illustrating an example of a configuration of an optical system of the fundus observation apparatus according to the ninth modification example of the embodiments.

FIG. 17B shows an another example of a configuration of an optical system of the fundus observation apparatus according to the ninth modification example of the embodiments. In FIG. 17B, like reference numerals designate like parts as in FIG. 10 or FIG. 17A. The same description may not be repeated.

The configuration of the optical system of the fundus observation apparatus 1m according to the present modification example differs from that of the optical system of the fundus observation apparatus 1c according to the second modification example in that the aspherical refractive optical element 35 is disposed between the first ellipsoidal mirror 40 and the second ellipsoidal mirror 50. In other words, the aspherical refractive optical element 35 is disposed on the optical path of the illumination light and the optical path of the returning light of the illumination light.

In the present modification example, when at least one of the first ellipsoidal mirror 40 and the second ellipsoidal mirror 50 is configured asymmetrically in the y direction with respect to the optical path (optical axis) of the illumination light or the returning light thereof, the aspherical refractive optical element 35 adds an aberration component asymmetric in the y direction with respect to the incident light. This allows to correct the aberration components of the first ellipsoidal mirror 40 and the second ellipsoidal mirror 50.

Figure 17C:
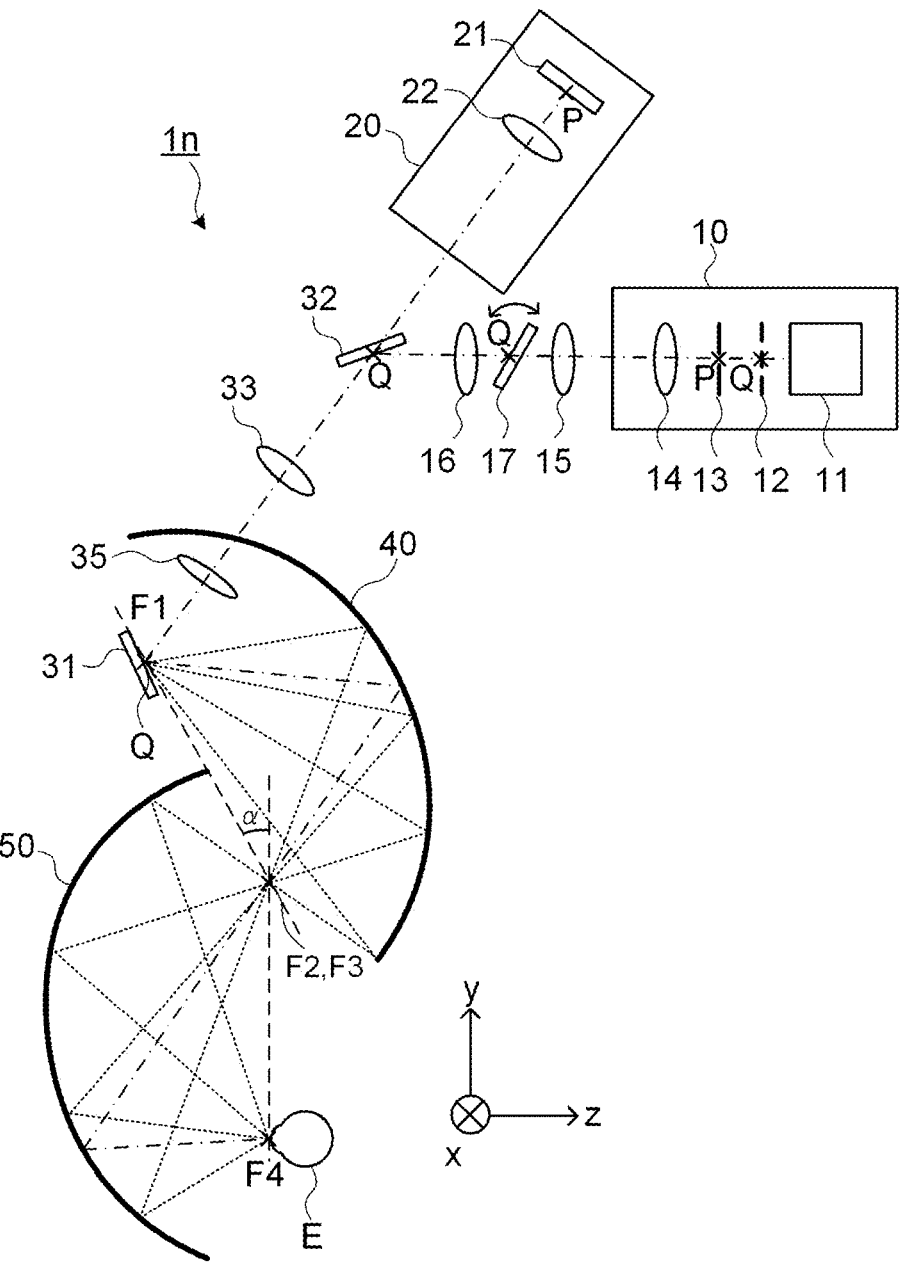
FIG. 17C is a schematic diagram illustrating an example of a configuration of an optical system of the fundus observation apparatus according to the ninth modification example of the embodiments.

FIG. 17C shows a still another example of a configuration of an optical system of the fundus observation apparatus according to the ninth modification example of the embodiments. In FIG. 17C, like reference numerals designate like parts as in FIG. 10 or FIG. 17A. The same description may not be repeated.

The configuration of the optical system of the fundus observation apparatus 1n according to the present modification example differs from that of the optical system of the fundus observation apparatus 1c according to the second modification example in that the aspherical refractive optical element 35 is disposed between the reflective mirror 31 and the relay lens 33. In other words, the aspherical refractive optical element 35 is disposed on the optical path of the illumination light and the optical path of the returning light of the illumination light.

In the present modification example, when at least one of the first ellipsoidal mirror 40 and the second ellipsoidal mirror 50 is configured asymmetrically in the y direction with respect to the optical path (optical axis) of the illumination light or the returning light thereof, each of the aspherical refractive optical elements 35 adds an aberration component asymmetric in the y direction with respect to the incident light. This allows to correct the aberration components of the first ellipsoidal mirror 40 and the second ellipsoidal mirror 50.

In the configuration shown in FIG. 11 or FIG. 15, one or more aspherical refractive optical elements may be disposed on the optical path of the illumination light and the optical path of the returning light of the illumination light, as in the present modification example. In the configuration shown in FIG. 15, when at least one of the hyperboloidal mirrors 42 and 43, and the ellipsoidal mirror 51 is configured asymmetrically in the y direction with respect to the optical path (optical axis) of the illumination light or the returning light thereof, the aspherical refractive optical element 35 adds an aberration component asymmetric in the y direction with respect to the incident light. This allows to correct the aberration components of the hyperboloidal mirrors 42 and 43, and the ellipsoidal mirror 51.

Further, in the configuration shown in FIG. 11, the aspherical refractive optical element 35 may be disposed between the dichroic mirror 90 and the OCT optical system 100. In some embodiments, the aspherical refractive optical element 35 is disposed only between the dichroic mirror 90 and the OCT optical system 100, without the aspherical refractive optical element 35 being disposed on the optical path of the illumination light and the optical path of the returning light of the illumination light.

The case where the aberrations in the y direction are corrected has been described in the present modification example. However, aberrations in the x direction may be corrected. Further, when the aspheric mirror described above is configured to be asymmetric in the x and y directions, the aberrations in the x and y directions may be corrected.

Tenth Modification Example

In the embodiments described above or the modification examples thereof, the case where the opening is formed in the region including the center part through which the optical axis passes in the hole mirror 30 has been described. However, the configuration according to the embodiments is not limited to this.

Figure 18:
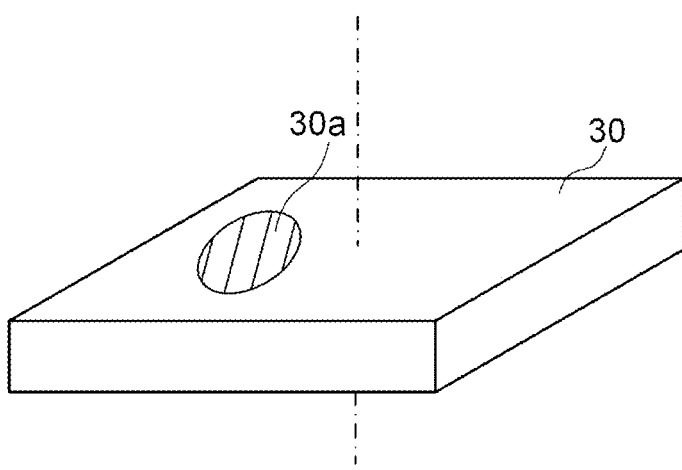
FIG. 18 is a schematic diagram illustrating an example of a configuration of an optical system of the fundus observation apparatus according to a tenth modification example of the embodiments.

FIG. 18 schematically shows a configuration of the hole mirror 30 according to a tenth modification example of the embodiments. In FIG. 18, parts similar to those in FIG. 12A are denoted by the same reference symbols, and description thereof is omitted as appropriate.

As shown in FIG. 18, the hole 30a is formed at a position eccentric from the optical axis in the hole mirror 30. In other words, the hole 30a is formed in the peripheral region of the region including the center part through which the optical axis passes. In this case, the fundus observation apparatus is configured so that the illumination light reflected on the peripheral region in the hole mirror 30 is guided to the subject's eye E, and that the returning light of the illumination light from the subject's eye E passes through the hole 30a formed at the position eccentric from the optical axis.

Eleventh Modification Example

In the embodiments described above or the modification example thereof, a case where the illumination light is configured to be reflected on the peripheral region of the region including the center part of the hole mirror 30 as the deflecting member and the returning light of the illumination light is configured to pass through the hole formed in the region including the center part of the hole mirror 30 has been described. However, the configuration according to the embodiments is not limited to this. For example, the illumination light may be reflected in the region including the center part of the deflecting member, and the returning light of the illumination light may be transmitted through (passed through) the peripheral region of the region including the center part of the deflecting member.

Figure 19:
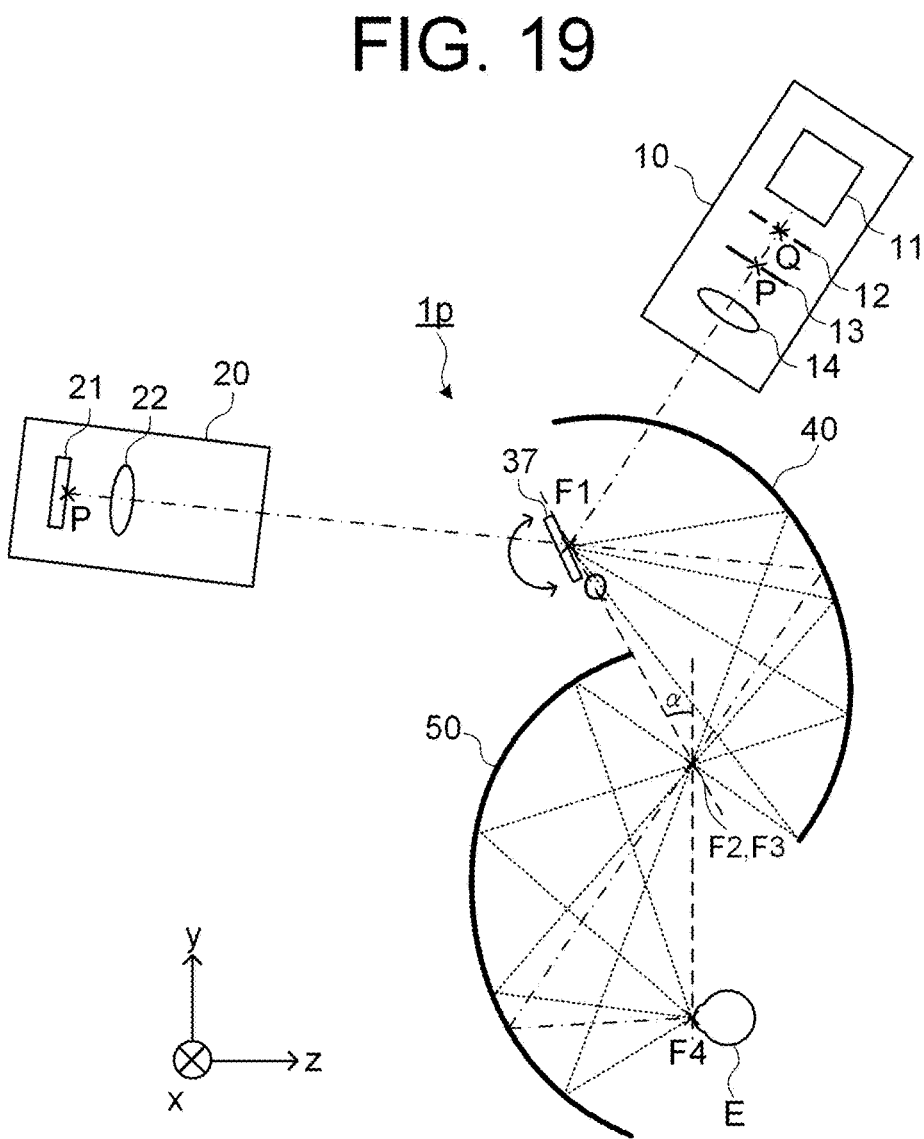
FIG. 19 is a schematic diagram illustrating an example of a configuration of an optical system of the fundus observation apparatus according to an eleventh modification example of the embodiments.

FIG. 19 shows an example of a configuration of an optical system of the fundus observation apparatus according to the eleventh modification example of the embodiments. In FIG. 19, like reference numerals designate like parts as in FIG. 1. The same description may not be repeated.

The configuration of the fundus observation apparatus 1p according to the eleventh modification example differs from that of the fundus observation apparatus 1 according to the first embodiment in that a deflecting mirror 37 as the deflecting member is provided instead of the hole mirror 30.

The deflecting mirror 37 (specifically, deflection surface described below) can be arranged at the pupil conjugate position Q. The deflecting mirror 37, similar to the hole mirror 30, has a deflection surface whose orientation (deflection direction) can be changed, and functions as a uniaxial optical scanner that guides the illumination light from the slit projection optical system 10 to the reflective surface of the first ellipsoidal mirror 40 described below.

Figure 20:
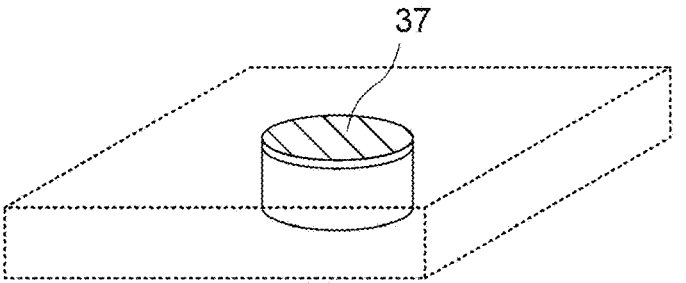
FIG. 20 is a schematic diagram illustrating an example of a configuration of an optical system of the fundus observation apparatus according to the eleventh modification example of the embodiments.

FIG. 20 schematically shows a configuration of the deflecting mirror 37 according to the eleventh modification example of the embodiments.

As shown in FIG. 20, the deflecting mirror 37 has a deflection surface with a reflective member. The deflecting mirror 37 has a configuration that reflects the illumination light on the deflection surface and transmits (passes through) the returning light of the illumination light in the periphery of the deflection surface. In this case, the illumination light is reflected on the region including the center part of the deflecting mirror 37, and the returning light of the illumination light passes through the peripheral region of the region including the center part of the deflecting mirror 37.

The deflecting mirror 37 deflects the illumination light by changing the orientation of the deflection surface so that the irradiated region moves sequentially in a direction (direction of the slit width, shorter direction of the irradiated region) orthogonal to the slit direction (direction in which the slit extends, longitudinal direction of the irradiated region) of the irradiated region at an irradiated site of the illumination light on the subject's eye E. The deflecting mirror 37 is configured to be capable of changing the deflection direction of the illumination light, under the control from the controller.

The illumination light from the slit projection optical system 10 is deflected on the deflection surface and is guided to the reflective surface of the first ellipsoidal mirror 40. The returning light of the illumination light from the subject's eye E passes through the peripheral region of the deflection surface of the deflecting mirror 37 via the reflective surface of the first ellipsoidal mirror 40, and is guided to the slit light receiving optical system 20.

Figure 21A:
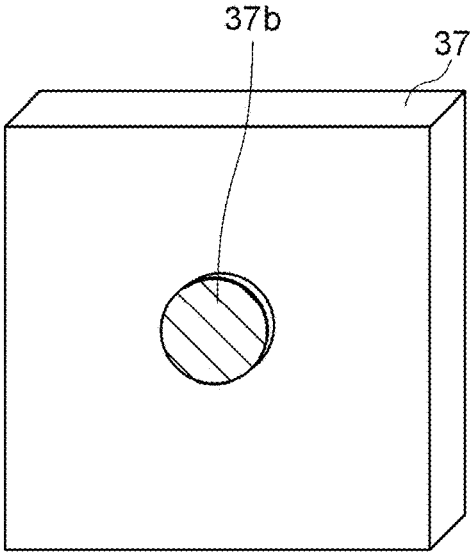
FIG. 21A is a schematic diagram illustrating an example of a configuration of an optical system of the fundus observation apparatus according to the eleventh modification example of the embodiments.
Figure 21B:
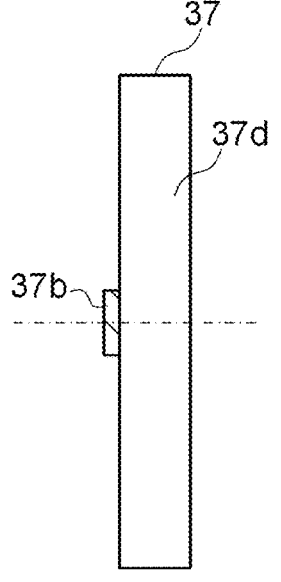
FIG. 21B is a schematic diagram illustrating an example of a configuration of an optical system of the fundus observation apparatus according to the eleventh modification example of the embodiments.

FIG. 21A and FIG. 21B schematically show another example of a configuration of the deflecting mirror 37 according to the eleventh modification example of the embodiments. FIG. 21A schematically represents an overview of the configuration of the deflecting mirror 37 according to the present modification example. FIG. 21B schematically represents the cross-sectional shape when cut in the cutting plane passing through the center of the deflecting mirror 37 in FIG. 21A.

As shown in FIG. 21A and FIG. 21B, the deflecting mirror 37 includes a plane parallel plate 37d made from a transmissive member through which at least the returning light of the illumination light can be transmitted, and a reflective film 37b provided on the surface of the plane parallel plate 37d. The reflective film 37b is formed on the center part through which the optical axis passes. For example, the reflective film 37b is formed by evaporating a metal film or a dielectric multi-layer onto the surface of the plane parallel plate 37d.

In some embodiments, as in the eighth modification example, the deflecting mirror 37 is disposed at a position eccentric from the optical axis.

Figure 22:
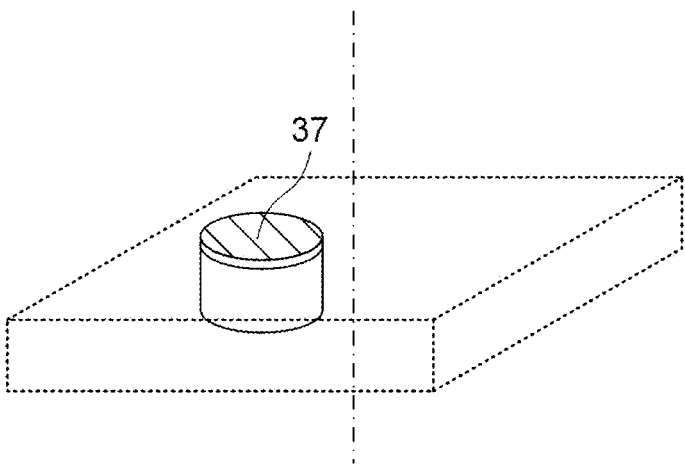
FIG. 22 is a schematic diagram illustrating an example of a configuration of an optical system of the fundus observation apparatus according to the eleventh modification example of the embodiments.

FIG. 22 schematically shows an another example of a configuration of the deflecting mirror 37 according to the eleventh modification example of the embodiments.

As shown in FIG. 22, the deflecting mirror 37 is disposed at a position eccentric from the optical axis. In this case, the fundus observation apparatus is configured so that the illumination light reflected on the deflection surface of the deflecting mirror 37 is guided to the subject's eye E, and that the returning light of the illumination light from the subject's eye E passes through the peripheral region of the deflection surface.

[Actions]

The fundus observation apparatus according to the embodiments will be described.

A fundus observation apparatus (1, 1a, 1b, 1e, 1g, 1h, 1j, 1p) includes an illumination optical system (slit projection optical system 10), a two-dimensional image sensor (image sensor 21), and a deflecting member (hole mirror 30, deflecting mirror 37). The illumination optical system is configured to illuminate a fundus (Ef) of a subject's eye (E) with line-shaped illumination light. The two-dimensional image sensor is configured to receive returning light of the illumination light from the fundus on a movable focal plane at a position substantially conjugate optically to the fundus (fundus conjugate position P). The deflecting member is configured to couple an optical path of the illumination light and an optical path of the returning light and to scan the fundus with the illumination light by deflecting the illumination light in synchronization with a movement of the focal plane. The deflecting member has a configuration that allows the returning light to be transmitted through a first region and to reflect the illumination light in a second region different from the first region.

The second region may be a region that does not overlap with the first region. According to such a configuration, the optical path of the illumination light and the optical path of the returning light of the illumination light from the fundus are coupled using the deflecting member, and the illumination light is deflected using the deflecting member to scan the fundus. Thereby, a shared optical system shared between the optical path of the wide-angle illumination light and the optical path of the returning light can be easily arranged while ensuring a wide-angle angle of view for imaging with the optical system alone that scans in a width direction of a line of the illumination light, with a low cost and simple configuration. Further, the optical system can also be arranged on the transmitting side of the deflecting member. Therefore, the configuration does not require a pupil relay system, thereby increasing the degree of freedom in the arrangement of the optical system.

In the fundus observation apparatus according to some embodiments, the two-dimensional image sensor is an image sensor using a rolling shutter method.

According to such a configuration, the fundus can be observed with high contrast, with a simple configuration.

In the fundus observation apparatus according to some embodiments, an optical path coupling part between the optical path of the illumination light and the optical path of the returning light is positioned at a position substantially conjugate optically to a pupil of the subject's eye (pupil conjugate position Q).

According to such a configuration, the illumination light can be efficiently incident in the eye. Thereby, the fundus can be observed with higher contrast.

In the fundus observation apparatus according to some embodiments, an angle of view for imaging is 80 degrees or more.

According to such a configuration, the fundus can be observed at a wide angle of view of 80 degrees or more with a low cost and simple configuration.

The fundus observation apparatus according to some embodiments further includes: an OCT optical system (100) including an optical scanner (150) and configured to perform OCT scan that irradiates measurement light (LS) deflected by the optical scanner onto the subject's eye and detects interference light (LC) between returning light of the measurement light and reference light (LR); and an optical path coupling separating member (dichroic mirror 90) arranged between the deflecting member and the two-dimensional image sensor and configured to couple the optical path of the returning light and an optical path of the OCT optical system.

According to such a configuration, by optically coupling the OCT optical system on the transmission side of the deflecting member, the optical path of the wide-angle illumination optical path and the optical path of the returning light of the illumination light can be separated at a low cost. Further, OCT measurement can be performed on any position of the fundus being observed at a large wide angle, without sharing an optical scanner for OCT scanning and an optical scanner for deflection of the illumination light.

In the fundus observation apparatus according to some embodiments, the illumination optical system includes a slit

(13) configured to be irradiated with light from an illumination light source (11) and to be capable of being arranged at a position substantially conjugate optically to the fundus of the subject's eye.

According to such a configuration, the illumination light whose luminous flux cross-sectional shape is a line shaped can be irradiated onto the fundus with a simple configuration.

A fundus observation apparatus (1b) according to some embodiments includes a fundus observation optical system (slit projection optical system 10 and slit light receiving optical system 20), an OCT optical system (100), and an optical path coupling separating member (dichroic mirror 90). The fundus observation optical system is configured to illuminate a fundus (Ef) of a subject's eye (E) with illumination light, and to receive returning light of the illumination light from the fundus using a two-dimensional image sensor (image sensor 21). The OCT optical system includes an optical scanner (150) and is configured to perform OCT scan that irradiates measurement light (LS) deflected by the optical scanner onto the subject's eye and detects interference light (LC) between returning light of the measurement light and reference light (LR). The optical path coupling separating member is configured to couple an optical path of the returning light of the illumination light with an optical path of the OCT optical system. The fundus observation optical system includes a deflecting member (hole mirror 30, deflecting mirror 37) having a configuration that allows the returning light to be transmitted through a first region and to reflect the illumination light in a second region different from the first region, and having a scanning mechanism that scans the fundus with the illumination light by deflecting the illumination light. The optical path coupling separating member is positioned between the deflecting member and the two-dimensional image sensor.

The second region may be a region that does not overlap with the first region. According to such a configuration, the optical path of the illumination light and the optical path of the returning light of the illumination light from the fundus are coupled using the deflecting member, and the illumination light is deflected using the deflecting member to scan the fundus. Thereby, a shared optical system shared between the optical path of the wide-angle illumination light and the optical path of the returning light can be easily arranged while ensuring a wide-angle angle of view for imaging, with a low cost and simple configuration. Further, by optically coupling the OCT optical system on the transmission side of the deflecting member, the optical path of the wide-angle illumination light source and the optical path of the returning light of the illumination light can be separated at a low cost. Further, OCT measurement can be performed on any position of the fundus being observed at a large wide angle, without sharing an optical scanner for OCT scanning and an optical scanner for deflection of the illumination light.

The fundus observing apparatus according to some embodiments further includes: a first concave mirror (first ellipsoidal mirror 40) having a concave surface-shaped first reflective surface, and configured to reflect the illumination light deflected by the deflecting member; and a second concave mirror (second ellipsoidal mirror 50) having a concave surface-shaped second reflective surface, and configured to reflect the illumination light reflected on the first reflective surface on the second reflective surface and to guide the reflected light to the subject's eye. The deflecting member is configured to guide the returning light that has been guided via the first concave mirror and the second concave mirror to the two-dimensional image sensor.

According to such a configuration, the fundus can be scanned at a wide angle using the concave mirror at a low cost and with high accuracy. In particular, since a deflecting member that deflects the illumination light between the first concave mirror and the second concave mirror is not required, imaging can be performed up to an angle of view beyond 180 degrees without being limited by the scan range of the deflecting member.

In the fundus observation apparatus according to some embodiments, the first reflective surface is an elliptical surface, and the deflecting member is positioned at a first focal point (F1) of the first concave mirror or near the first focal point of the first concave mirror.

According to such a configuration, the fundus can be scanned at a wide angle using the ellipsoidal mirror at a low cost and with high accuracy.

In the fundus observation apparatus according to some embodiments, the second reflective surface is an elliptical surface, and the subject's eye is arranged at a first focal point (second focal point F4) of the second concave mirror or near the first focal point of the second concave mirror.

According to such a configuration, the fundus can be scanned at a wide angle using the ellipsoidal mirror at a low cost and with high accuracy.

In the fundus observation apparatus according to some embodiments, each of the first reflective surface and the second reflective surface is an elliptical surface, the deflecting member is positioned at a first focal point (F1) of the first concave mirror or near the first focal point of the first concave mirror, a second focal point (F2) of the first concave mirror is positioned so as to substantially coincide with a first focal point (F3) of the second concave mirror, and the subject's eye is arranged at a second focal point (F4) of the second concave mirror or near the second focal point of the second concave mirror.

According to such a configuration, the fundus can be scanned at a wide angle using the ellipsoidal mirror at a low cost and with high accuracy.

In the fundus observation apparatus according to some embodiments, at least one of the first concave mirror or the second concave mirror is asymmetrically configured in a first direction (y direction) intersecting the optical path of the illumination light. The fundus observation apparatus further includes an aspherical refractive optical element (35) arranged on at least one of the optical path of the illumination light or the optical path of the returning light and configured to correct aberration components in the first direction.

According to such a configuration, aberrations caused by asymmetry in the configuration of at least one of the first concave mirror and the second concave mirror can be corrected.

The fundus observation apparatus according to some embodiments further includes: a first concave mirror (hyperboloidal mirror 42) having a concave surface-shaped first reflective surface, and configured to reflect the illumination light deflected by the deflecting member; a convex mirror (hyperboloidal mirror 43) having a convex surface-shaped second reflective surface, and configured to reflect the illumination light reflected on the first reflective surface; and a second concave mirror (ellipsoidal mirror 51) having a concave surface-shaped third reflective surface, and configured to reflect the illumination light reflected on the second reflective surface on the third reflective surface and to guide the reflected light to the subject's eye. The deflecting member is configured to guide the returning light that has been guided via the first concave mirror, the convex mirror, and the second concave mirror to the two-dimensional image sensor.

According to such a configuration, the fundus can be scanned at a wide angle using the concave mirror at a low cost and with high accuracy. In particular, since a deflecting member that deflects the illumination light between the convex mirror and the second concave mirror is not required, imaging can be performed up to an angle of view beyond 180 degrees without being limited by the scan range of the deflecting member.

In the fundus observation apparatus according to some embodiments, the first reflective surface and the second reflective surface are hyperboloids, and the third reflective surface is an elliptical surface.

According to such a configuration, the fundus can be scanned at a wide angle using the two hyperboloidal mirrors and a single ellipsoidal at a low cost and with high accuracy.

In the fundus observation apparatus according to some embodiments, at least one of the first concave mirror, the convex mirror, or the second concave mirror is asymmetrically configured in a first direction (y direction) intersecting the optical path of the illumination light. The fundus observation apparatus further includes an aspherical refractive optical element (35) arranged on at least one of the optical path of the illumination light or the optical path of the returning light and configured to correct aberration components in the first direction.

According to such a configuration, aberrations caused by asymmetry in the configuration of at least one of the first concave mirror, the convex mirror and the second concave mirror can be corrected.

In the fundus observation apparatus according to some embodiments, a tapered hole is formed in the first region of the deflecting member so that an opening size on a light receiving side of the returning light is larger.

According to such a configuration, when the deflecting member is tilted, the occurrence of vignetting of the light flux of the returning light on the light receiving side can be suppressed.

In the fundus observation apparatus according to some embodiments, the first region is a region including a central part of the deflecting member, and the second region is a peripheral region of the first region in the deflecting member.

According to such a configuration, the optical path of the illumination light and the optical path of the returning light of the illumination light from the fundus are coupled and the illumination light can be deflected to scan the fundus, with a simple configuration.

In the fundus observation apparatus according to some embodiments, the first region is a peripheral region of a region including a central part of the deflecting member, and the second region is the region including the central part of the deflecting member.

According to such a configuration, the optical path of the illumination light and the optical path of the returning light of the illumination light from the fundus are coupled and the illumination light can be deflected to scan the fundus with a simple configuration.

OTHERS

The above-described embodiments are merely examples for carrying out the present invention. Those who intend to implement the present invention can apply any modification, omission, addition, or the like within the scope of the gist of the present invention.

In some embodiments, a program for causing a processor (computer) to execute the method of controlling the fundus observation apparatus described above is provided. Such a program can be stored in any non-transitory recording medium (storage medium) that can be read by a computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like. The computer program may be transmitted and received through a network such as the Internet, LAN, etc.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A fundus observation apparatus, comprising:
an illumination optical system configured to illuminate a fundus of a subject's eye with line-shaped illumination light;
a two-dimensional image sensor configured to receive returning light of the illumination light from the fundus on a movable focal plane at a position substantially conjugate optically to the fundus;
a deflecting member configured to couple an optical path of the illumination light and an optical path of the returning light and to scan the fundus with the illumination light by deflecting the illumination light in synchronization with a movement of the focal plane;
an OCT optical system including an optical scanner and configured to perform OCT scan that irradiates measurement light deflected by the optical scanner onto the subject's eye and detects interference light between returning light of the measurement light and reference light; and
an optical path coupling separating member arranged between the deflecting member and the two-dimensional image sensor and configured to couple the optical path of the returning light and an optical path of the OCT optical system,
wherein
the deflecting member has a configuration that allows the returning light to be transmitted through a first region and to reflect the illumination light in a second region different from the first region.

2. The fundus observation apparatus of claim 1, wherein the two-dimensional image sensor is an image sensor using a rolling shutter method.

3. The fundus observation apparatus of claim 1, wherein an optical path coupling part between the optical path of the illumination light and the optical path of the returning light is positioned at a position substantially conjugate optically to a pupil of the subject's eye.

4. The fundus observation apparatus of claim 1, wherein an angle of view for imaging is 80 degrees or more.

5. The fundus observation apparatus of claim 1, wherein the illumination optical system includes a slit configured to be irradiated with light from an illumination light source and to be capable of being arranged at a position substantially conjugate optically to the fundus of the subject's eye.

6. The fundus observation apparatus of claim 1, further comprising:

a first concave mirror having a concave surface-shaped first reflective surface, and configured to reflect the illumination light deflected by the deflecting member; and a second concave mirror having a concave surface-shaped second reflective surface, and configured to reflect the illumination light reflected on the first reflective surface on the second reflective surface and to guide the reflected light to the subject's eye, wherein the deflecting member is configured to guide the returning light that has been guided via the first concave mirror and the second concave mirror to the two-dimensional image sensor.

7. The fundus observation apparatus of claim 6, wherein the first reflective surface is an elliptical surface, and the deflecting member is positioned at a first focal point of the first concave mirror or near the first focal point of the first concave mirror.

8. The fundus observation apparatus of claim 6, wherein the second reflective surface is an elliptical surface, and the subject's eye is arranged at a first focal point of the second concave mirror or near the first focal point of the second concave mirror.

9. The fundus observation apparatus of claim 6, wherein each of the first reflective surface and the second reflective surface is an elliptical surface, the deflecting member is positioned at a first focal point of the first concave mirror or near the first focal point of the first concave mirror, a second focal point of the first concave mirror is positioned so as to substantially coincide with a first focal point of the second concave mirror, and the subject's eye is arranged at a second focal point of the second concave mirror or near the second focal point of the second concave mirror.

10. The fundus observation apparatus of claim 6, wherein at least one of the first concave mirror or the second concave mirror is asymmetrically configured in a first direction intersecting the optical path of the illumination light, and the fundus observation apparatus further includes an aspherical refractive optical element arranged on at least one of the optical path of the illumination light or the optical path of the returning light and configured to correct aberration components in the first direction.

11. The fundus observation apparatus of claim 1, wherein a tapered hole is formed in the first region of the deflecting member so that an opening size on a light receiving side of the returning light is larger.

12. The fundus observation apparatus of claim 1, wherein the first region is a region including a central part of the deflecting member, and

42 the second region is a peripheral region of the first region in the deflecting member.

13. The fundus observation apparatus of claim 1, wherein the first region is a peripheral region of a region including a central part of the deflecting member, and the second region is the region including the central part of the deflecting member.

14. A fundus observation apparatus, comprising:

an illumination optical system configured to illuminate a fundus of a subject's eye with line-shaped illumination light;

a two-dimensional image sensor configured to receive returning light of the illumination light from the fundus on a movable focal plane at a position substantially conjugate optically to the fundus;

a deflecting member configured to couple an optical path of the illumination light and an optical path of the returning light and to scan the fundus with the illumination light by deflecting the illumination light in synchronization with a movement of the focal plane;

a first concave mirror having a concave surface-shaped first reflective surface, and configured to reflect the illumination light deflected by the deflecting member;

a convex mirror having a convex surface-shaped second reflective surface, and configured to reflect the illumination light reflected on the first reflective surface; and a second concave mirror having a concave surface-shaped third reflective surface, and configured to reflect the illumination light reflected on the second reflective surface on the third reflective surface and to guide the reflected light to the subject's eye, wherein the deflecting member has a configuration that allows the returning light to be transmitted through a first region and to reflect the illumination light in a second region different from the first region, and the deflecting member is configured to guide the returning light that has been guided via the first concave mirror, the convex mirror, and the second concave mirror to the two-dimensional image sensor.

15. The fundus observation apparatus of claim 14, wherein the first reflective surface and the second reflective surface are hyperboloids, and the third reflective surface is an elliptical surface.

16. The fundus observation apparatus of claim 14, wherein at least one of the first concave mirror, the convex mirror, or the second concave mirror is asymmetrically configured in a first direction intersecting the optical path of the illumination light, and the fundus observation apparatus further include an aspherical refractive optical element arranged on at least one of the optical path of the illumination light or the optical path of the returning light and configured to correct aberration components in the first direction.

17. A fundus observation apparatus, comprising:

a fundus observation optical system configured to illuminate a fundus of a subject's eye with illumination light, and to receive returning light of the illumination light from the fundus using a two-dimensional image sensor;

an OCT optical system including an optical scanner and configured to perform OCT scan that irradiates measurement light deflected by the optical scanner onto the subject's eye and detects interference light between returning light of the measurement light and reference light;

an optical path coupling separating member configured to couple an optical path of the returning light of the illumination light with an optical path of the OCT optical system;

a first concave mirror having a concave surface-shaped first reflective surface, and configured to reflect the illumination light deflected by the deflecting member; and a second concave mirror having a concave surface-shaped second reflective surface, and configured to reflect the illumination light reflected on the first reflective surface on the second reflective surface and to guide the reflected light to the subject's eye, wherein the fundus observation optical system includes a deflecting member having a configuration that allows the returning light to be transmitted through a first region and to reflect the illumination light in a second region different from the first region, and having a scanning mechanism that scans the fundus with the illumination light by deflecting the illumination light, wherein the optical path coupling separating member is positioned between the deflecting member and the two-dimensional image sensor, and the deflecting member is configured to guide the returning light that has been guided via the first concave mirror and the second concave mirror to the two-dimensional image sensor.

18. A fundus observation apparatus, comprising:

a fundus observation optical system configured to illuminate a fundus of a subject's eye with illumination light, and to receive returning light of the illumination light from the fundus using a two-dimensional image sensor;

an OCT optical system including an optical scanner and configured to perform OCT scan that irradiates measurement light deflected by the optical scanner onto the subject's eye and detects interference light between returning light of the measurement light and reference light;

an optical path coupling separating member configured to couple an optical path of the returning light of the illumination light with an optical path of the OCT optical system;

a first concave mirror having a concave surface-shaped first reflective surface, and configured to reflect the illumination light deflected by the deflecting member;

a convex mirror having a convex surface-shaped second reflective surface, and configured to reflect the illumination light reflected on the first reflective surface; and a second concave mirror having a concave surface-shaped third reflective surface, and configured to reflect the illumination light reflected on the second reflective surface on the third reflective surface and to guide the reflected light to the subject's eye, wherein the fundus observation optical system includes a deflecting member having a configuration that allows the returning light to be transmitted through a first region and to reflect the illumination light in a second region different from the first region, and having a scanning mechanism that scans the fundus with the illumination light by deflecting the illumination light, wherein the optical path coupling separating member is positioned between the deflecting member and the two-dimensional image sensor, and the deflecting member is configured to guide the returning light that has been guided via the first concave mirror, the convex mirror, and the second concave mirror to the two-dimensional image sensor.

\* \* \* \* \*